US010201584B1

United States Patent
Collins et al.

(10) Patent No.: US 10,201,584 B1
(45) Date of Patent: *Feb. 12, 2019

(54) COMPOSITIONS AND METHODS FOR TREATING HCV

(71) Applicant: AbbVie Inc., North Chicago, IL (US)

(72) Inventors: Christine A. Collins, Skokie, IL (US); Daniel E. Cohen, Highland Park, IL (US); Gennadiy Koev, Libertyville, IL (US); Preethi Krishnan, Gurnee, IL (US); Tami J. Pilot-Matias, Green Oaks, IL (US)

(73) Assignee: ABBVIE INC., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/247,975

(22) Filed: Apr. 8, 2014

Related U.S. Application Data

(63) Continuation of application No. 13/474,411, filed on May 17, 2012, now abandoned.

(60) Provisional application No. 61/486,842, filed on May 17, 2011.

(51) Int. Cl.

| | | |
|---|---|---|
| *A01N 37/18* | (2006.01) |
| *A61K 38/00* | (2006.01) |
| *A61K 31/33* | (2006.01) |
| *A61K 31/00* | (2006.01) |
| *A61K 31/505* | (2006.01) |
| *A61K 31/435* | (2006.01) |
| *A61K 31/44* | (2006.01) |
| *A61K 31/41* | (2006.01) |
| *A61K 31/40* | (2006.01) |
| *A61K 31/27* | (2006.01) |
| *A61K 31/16* | (2006.01) |
| *A01N 43/00* | (2006.01) |
| *A01N 43/58* | (2006.01) |
| *A01N 43/54* | (2006.01) |
| *A01N 43/40* | (2006.01) |
| *A01N 43/42* | (2006.01) |
| *A01N 43/64* | (2006.01) |
| *A01N 43/36* | (2006.01) |
| *A01N 43/38* | (2006.01) |
| *A01N 47/10* | (2006.01) |
| *A01N 41/02* | (2006.01) |
| *C07D 471/04* | (2006.01) |
| *C07D 471/22* | (2006.01) |
| *C07D 487/04* | (2006.01) |
| *A61P 1/16* | (2006.01) |
| *A61K 38/05* | (2006.01) |
| *A61K 31/513* | (2006.01) |
| *A61K 45/06* | (2006.01) |

(52) U.S. Cl.
CPC .............. *A61K 38/05* (2013.01); *A01N 37/18* (2013.01); *A61K 31/513* (2013.01); *A61K 38/00* (2013.01); *A61K 45/06* (2013.01)

(58) Field of Classification Search
None
See application file for complete search history.

(56) References Cited

U.S. PATENT DOCUMENTS

| | | |
|---|---|---|
| 5,541,206 A | 7/1996 | Kempf et al. |
| 5,830,867 A | 11/1998 | Bhatnagar et al. |
| 5,831,002 A | 11/1998 | Haupt et al. |
| 5,935,982 A | 8/1999 | Dykstra et al. |
| 6,042,847 A | 3/2000 | Kerc et al. |
| 6,235,493 B1 | 5/2001 | Bissell et al. |
| 6,268,207 B1 | 7/2001 | Bailey |
| 6,323,180 B1 | 11/2001 | Llinas-Brunet et al. |
| 6,329,379 B1 | 12/2001 | Llinas-Brunet et al. |
| 6,329,417 B1 | 12/2001 | Llinas-Brunet et al. |
| 6,369,091 B1 | 4/2002 | Sircar et al. |
| 6,388,093 B1 | 5/2002 | Chamberlain et al. |
| 6,410,531 B1 | 6/2002 | Llinas-Brunet et al. |
| 6,420,380 B2 | 7/2002 | Llinas-Brunet et al. |
| 6,534,523 B1 | 3/2003 | Llinas-Brunet et al. |
| 6,599,528 B1 | 7/2003 | Rosenberg et al. |
| 6,608,027 B1 | 8/2003 | Tsantrizos et al. |
| 6,642,204 B2 | 11/2003 | Llinas-Brunet et al. |
| 6,653,295 B2 | 11/2003 | Glunz et al. |
| 6,699,855 B2 | 3/2004 | Zhang et al. |
| 6,703,403 B2 | 3/2004 | Norbeck et al. |
| 6,727,366 B2 | 4/2004 | Han et al. |
| 6,767,991 B1 | 7/2004 | Llinas-Brunet et al. |

(Continued)

FOREIGN PATENT DOCUMENTS

| | | |
|---|---|---|
| BR | PI0401908 A | 1/2006 |
| DE | 75755 C | 6/1894 |

(Continued)

OTHER PUBLICATIONS

AbbVie, "DDW 2014: AbbVie interferon-free regimen cures more than 90% of hepatitis C patients," available online at http://www.eatg.org/?module=mobi&action=news_details&id=170229, 4 pages (2014).*

(Continued)

*Primary Examiner* — James H Alstrum-Acevedo
*Assistant Examiner* — Thea D'Ambrosio
(74) *Attorney, Agent, or Firm* — Neal, Gerber & Eisenberg LLP

(57) ABSTRACT

This disclosure is directed to pharmaceutical compositions that comprise two or more therapeutic agents that, inter alia, are useful for inhibiting hepatitis C virus (HCV) and methods for inhibiting HCV by co-administering two or more anti-HCV therapeutic agents.

13 Claims, 3 Drawing Sheets

(56) References Cited

U.S. PATENT DOCUMENTS

| | | |
|---|---|---|
| 6,774,212 B2 | 8/2004 | Han |
| 6,803,374 B2 | 10/2004 | Priestley et al. |
| 6,846,802 B2 | 1/2005 | Chen et al. |
| 6,846,806 B2 | 1/2005 | Priestley |
| 6,867,185 B2 | 3/2005 | Campbell et al. |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,881,741 B2 | 4/2005 | Chan Chun Kong et al. |
| 6,919,366 B2 | 7/2005 | Sircar et al. |
| 6,923,988 B2 | 8/2005 | Patel et al. |
| 6,939,854 B2 | 9/2005 | Priestley |
| 6,995,174 B2 | 2/2006 | Wang et al. |
| 7,037,911 B2 | 5/2006 | Zhang |
| 7,041,698 B2 | 5/2006 | Ripka et al. |
| 7,065,453 B1 | 6/2006 | Diller et al. |
| 7,091,184 B2 | 8/2006 | Llinas-Brunet et al. |
| 7,108,864 B1 | 9/2006 | Martino et al. |
| 7,112,601 B2 | 9/2006 | Glunz et al. |
| 7,119,072 B2 | 10/2006 | Llinas-Brunet et al. |
| 7,122,627 B2 | 10/2006 | Priestley et al. |
| 7,132,504 B2 | 11/2006 | Scola et al. |
| 7,135,462 B2 | 11/2006 | Scola et al. |
| 7,141,574 B2 | 11/2006 | Beaulieu et al. |
| 7,153,848 B2 | 12/2006 | Hudyma et al. |
| 7,157,424 B2 | 1/2007 | Chen et al. |
| 7,173,004 B2 | 2/2007 | McPhee et al. |
| 7,176,208 B2 | 2/2007 | Nakajima et al. |
| 7,183,270 B2 | 2/2007 | Cherney et al. |
| 7,183,302 B2 | 2/2007 | Romine et al. |
| 7,189,844 B2 | 3/2007 | Gallou et al. |
| 7,309,708 B2 | 12/2007 | Tu et al. |
| 7,323,447 B2 | 1/2008 | Sin et al. |
| 7,348,425 B2 | 3/2008 | Hudyma et al. |
| 7,368,452 B2 | 5/2008 | Nakajima et al. |
| 7,375,218 B2 | 5/2008 | Gallou |
| 7,488,832 B2 | 2/2009 | Cole et al. |
| 7,491,794 B2 | 2/2009 | Blatt et al. |
| 7,504,378 B2 | 3/2009 | Llinas-Brunet et al. |
| 7,544,798 B2 | 6/2009 | Busacca et al. |
| 7,566,719 B2 | 7/2009 | Nakajima et al. |
| 7,592,419 B2 | 9/2009 | Venkatraman et al. |
| 7,601,709 B2 | 10/2009 | Miao et al. |
| 7,608,590 B2 | 10/2009 | Rosenquist et al. |
| 7,642,235 B2 | 1/2010 | Llinas-Brunet et al. |
| 7,642,339 B2 | 1/2010 | Chaudhary et al. |
| 7,659,245 B2 | 2/2010 | Simmen et al. |
| 7,659,270 B2 | 2/2010 | Bachand et al. |
| 7,687,459 B2 | 3/2010 | Niu et al. |
| 7,704,992 B2 | 4/2010 | Bachand et al. |
| 7,728,027 B2 | 6/2010 | Pack et al. |
| 7,732,457 B2 | 6/2010 | Malamas et al. |
| 7,741,281 B2 | 6/2010 | D'Andrea et al. |
| 7,741,347 B2 | 6/2010 | Bachand et al. |
| 7,745,636 B2 | 6/2010 | Bachand et al. |
| 7,759,495 B2 | 7/2010 | Bachand et al. |
| 7,763,584 B2 | 7/2010 | Wang et al. |
| 7,763,731 B2 | 7/2010 | Rockway et al. |
| 7,772,180 B2 | 8/2010 | Sin et al. |
| 7,772,183 B2 | 8/2010 | Carini et al. |
| 7,829,665 B2 | 11/2010 | Blatt et al. |
| 7,838,711 B2 | 11/2010 | Herweck et al. |
| 7,906,655 B2 | 3/2011 | Belema et al. |
| 8,025,899 B2 | 9/2011 | Berndl et al. |
| 8,101,643 B2 | 1/2012 | Qiu et al. |
| 8,188,104 B2 | 5/2012 | Flentge et al. |
| 8,202,912 B2 | 6/2012 | Curatolo et al. |
| 8,268,349 B2 | 9/2012 | Rosenberg et al. |
| 8,415,315 B2 | 4/2013 | Chakrabarti |
| 8,466,159 B2 * | 6/2013 | Bernstein et al. ....... 514/255.05 |
| 8,476,225 B2 | 7/2013 | Casarez et al. |
| 8,492,386 B2 * | 7/2013 | Bernstein et al. ....... 514/255.05 |
| 8,501,238 B2 | 8/2013 | Flentge et al. |
| 8,642,538 B2 | 2/2014 | Ku et al. |
| 8,680,106 B2 | 3/2014 | Bernstein et al. |
| 8,685,984 B2 * | 4/2014 | Bernstein et al. ....... 514/255.05 |
| 8,686,026 B2 | 4/2014 | Liepold et al. |
| 8,691,938 B2 * | 4/2014 | DeGoey et al. .............. 530/206 |
| 8,809,265 B2 * | 8/2014 | Bernstein et al. ............. 514/4.3 |
| 8,853,176 B2 * | 10/2014 | Bernstein et al. ............... 514/43 |
| 8,969,357 B2 * | 3/2015 | Bernstein et al. ....... 514/255.05 |
| 8,993,578 B2 * | 3/2015 | Bernstein et al. ....... 514/255.05 |
| 9,006,387 B2 | 4/2015 | Wagner et al. |
| 9,139,536 B2 | 9/2015 | Flentge et al. |
| 9,333,204 B2 | 5/2016 | Miller et al. |
| 9,629,841 B2 | 4/2017 | Li et al. |
| 9,744,170 B2 | 8/2017 | Miller et al. |
| 2002/0016442 A1 | 2/2002 | Llinas-Brunet et al. |
| 2002/0037998 A1 | 3/2002 | Llinas-Brunet et al. |
| 2002/0111313 A1 | 8/2002 | Campbell et al. |
| 2002/0183319 A1 | 12/2002 | Liang et al. |
| 2003/0004203 A1 | 1/2003 | Sircar et al. |
| 2003/0100582 A1 | 5/2003 | Sircar et al. |
| 2003/0181363 A1 | 9/2003 | Llinas-Brunet et al. |
| 2003/0186895 A1 | 10/2003 | Llinas-Brunet et al. |
| 2003/0187018 A1 | 10/2003 | Llinas-Brunet et al. |
| 2003/0191067 A1 | 10/2003 | Llinas-Brunet et al. |
| 2003/0195228 A1 | 10/2003 | Chen et al. |
| 2003/0224977 A1 | 12/2003 | Llinas-Brunet et al. |
| 2003/0232386 A1 | 12/2003 | Shah et al. |
| 2004/0002448 A1 | 1/2004 | Tsantrizos et al. |
| 2004/0013697 A1 | 1/2004 | Berndl et al. |
| 2004/0038872 A1 | 2/2004 | Campbell et al. |
| 2004/0048802 A1 | 3/2004 | Ripka et al. |
| 2004/0058982 A1 | 3/2004 | Harris |
| 2004/0072243 A1 | 4/2004 | Sands et al. |
| 2004/0106559 A1 | 6/2004 | Wang et al. |
| 2004/0180815 A1 | 9/2004 | Nakajima et al. |
| 2004/0229776 A1 | 11/2004 | Chen et al. |
| 2004/0229777 A1 | 11/2004 | Cerreta et al. |
| 2004/0229818 A1 | 11/2004 | Llinas-Brunet |
| 2004/0248779 A1 | 12/2004 | Dersch et al. |
| 2004/0248806 A1 | 12/2004 | Temsamani et al. |
| 2004/0266668 A1 | 12/2004 | Nakajima et al. |
| 2005/0020503 A1 | 1/2005 | Llinas-Brunet et al. |
| 2005/0049187 A1 | 3/2005 | Brandenburg et al. |
| 2005/0075279 A1 | 4/2005 | Llinas-Brunet et al. |
| 2005/0075343 A1 | 4/2005 | Sircar et al. |
| 2005/0080005 A1 | 4/2005 | Llinas-Brunet et al. |
| 2005/0084529 A1 | 4/2005 | Rosenberg et al. |
| 2005/0090432 A1 | 4/2005 | McPhee et al. |
| 2005/0119168 A1 | 6/2005 | Venkatraman et al. |
| 2005/0143316 A1 | 6/2005 | Tu et al. |
| 2005/0148085 A1 | 7/2005 | Larsen |
| 2005/0153877 A1 | 7/2005 | Miao et al. |
| 2005/0153900 A1 | 7/2005 | Velazquez et al. |
| 2005/0164921 A1 | 7/2005 | Njoroge et al. |
| 2005/0192212 A1 | 9/2005 | Llinas-Brunet et al. |
| 2005/0197375 A1 | 9/2005 | Sircar et al. |
| 2005/0209135 A1 | 9/2005 | Busacca et al. |
| 2005/0214366 A1 | 9/2005 | Harris |
| 2005/0215423 A1 | 9/2005 | Brenner et al. |
| 2005/0222045 A1 | 10/2005 | Auvin et al. |
| 2005/0267018 A1 | 12/2005 | Blatt et al. |
| 2005/0267151 A1 | 12/2005 | Busacca et al. |
| 2006/0003942 A1 | 1/2006 | Tung et al. |
| 2006/0009667 A1 | 1/2006 | Herweck et al. |
| 2006/0019905 A1 | 1/2006 | Bailey et al. |
| 2006/0046965 A1 | 3/2006 | Bailey et al. |
| 2006/0052602 A1 | 3/2006 | Kim et al. |
| 2006/0058317 A1 | 3/2006 | Gravestock et al. |
| 2006/0063915 A1 | 3/2006 | Gallou et al. |
| 2006/0063916 A1 | 3/2006 | Gallou |
| 2006/0068007 A1 | 3/2006 | Li et al. |
| 2006/0089300 A1 | 4/2006 | Llinas-Brunet et al. |
| 2006/0105997 A1 | 5/2006 | Arrington et al. |
| 2006/0122123 A1 | 6/2006 | Chaudhary et al. |
| 2006/0166893 A1 | 7/2006 | Auvin et al. |
| 2006/0172950 A1 | 8/2006 | Wang et al. |
| 2006/0199773 A1 | 9/2006 | Sausker et al. |
| 2006/0205638 A1 | 9/2006 | Busacca et al. |
| 2006/0257980 A1 | 11/2006 | Li |
| 2006/0258868 A1 | 11/2006 | Bailey et al. |
| 2006/0263433 A1 | 11/2006 | Ayer et al. |

(56) References Cited

U.S. PATENT DOCUMENTS

| | | |
|---|---|---|
| 2006/0275366 A1 | 12/2006 | Malcolm et al. |
| 2006/0276405 A1 | 12/2006 | Albrecht |
| 2006/0276407 A1 | 12/2006 | Albrecht et al. |
| 2006/0281688 A1 | 12/2006 | Zhang et al. |
| 2007/0004635 A1 | 1/2007 | Albrecht et al. |
| 2007/0004741 A1 | 1/2007 | Apodaca et al. |
| 2007/0010431 A1 | 1/2007 | Malcolm et al. |
| 2007/0010455 A1 | 1/2007 | Hewawasam et al. |
| 2007/0060510 A1 | 3/2007 | Nakajima et al. |
| 2007/0060565 A1 | 3/2007 | Meanwell et al. |
| 2007/0072809 A1 | 3/2007 | Cho et al. |
| 2007/0078081 A1 | 4/2007 | Casarez et al. |
| 2007/0078122 A1 | 4/2007 | Bergstrom et al. |
| 2007/0093414 A1 | 4/2007 | Carini et al. |
| 2007/0099825 A1 | 5/2007 | D'Andrea et al. |
| 2007/0142434 A1 | 6/2007 | Sandanayaka et al. |
| 2007/0161575 A1 | 7/2007 | Miao et al. |
| 2007/0179167 A1 | 8/2007 | Cottrell et al. |
| 2007/0184024 A1 | 8/2007 | Meanwell et al. |
| 2007/0185083 A1 | 8/2007 | Bergstrom et al. |
| 2007/0197558 A1 | 8/2007 | Betebenner et al. |
| 2007/0232627 A1 | 10/2007 | Betebenner et al. |
| 2007/0232645 A1 | 10/2007 | Rockway et al. |
| 2007/0237818 A1 | 10/2007 | Malcolm et al. |
| 2007/0243166 A1 | 10/2007 | Llinas-Brunet et al. |
| 2007/0249637 A1 | 10/2007 | Collins et al. |
| 2007/0258947 A1 | 11/2007 | Njoroge et al. |
| 2007/0270405 A1 | 11/2007 | Bender et al. |
| 2007/0270406 A1 | 11/2007 | Gentles et al. |
| 2007/0275930 A1 | 11/2007 | Gentles et al. |
| 2007/0281884 A1 | 12/2007 | Sun et al. |
| 2007/0281885 A1 | 12/2007 | Sun et al. |
| 2007/0287664 A1 | 12/2007 | Ralston et al. |
| 2007/0287694 A1 | 12/2007 | Yeung et al. |
| 2007/0299068 A1 | 12/2007 | Karp et al. |
| 2007/0299078 A1 | 12/2007 | Niu et al. |
| 2008/0008681 A1 | 1/2008 | Niu et al. |
| 2008/0014173 A1 | 1/2008 | Scola et al. |
| 2008/0032936 A1 | 2/2008 | Gai et al. |
| 2008/0038225 A1 | 2/2008 | Sun et al. |
| 2008/0039375 A1 | 2/2008 | Moore et al. |
| 2008/0039470 A1 | 2/2008 | Niu et al. |
| 2008/0044379 A1 | 2/2008 | Bachand et al. |
| 2008/0044380 A1 | 2/2008 | Bachand et al. |
| 2008/0045536 A1 | 2/2008 | Vaccaro et al. |
| 2008/0050336 A1 | 2/2008 | Bachand et al. |
| 2008/0075696 A1 | 3/2008 | Parsons et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0108632 A1 | 5/2008 | Lin et al. |
| 2008/0119461 A1 | 5/2008 | Sin et al. |
| 2008/0145334 A1 | 6/2008 | Wang et al. |
| 2008/0146537 A1 | 6/2008 | Bender et al. |
| 2008/0152619 A1 | 6/2008 | Sin et al. |
| 2008/0152622 A1 | 6/2008 | Nakajima et al. |
| 2008/0159982 A1 | 7/2008 | Wang et al. |
| 2008/0171015 A1 | 7/2008 | Bender et al. |
| 2008/0181868 A1 | 7/2008 | Sun et al. |
| 2008/0188494 A1 | 8/2008 | Dietz et al. |
| 2008/0200497 A1 | 8/2008 | Bailey et al. |
| 2008/0221107 A1 | 9/2008 | Giordanetto et al. |
| 2008/0242835 A1 | 10/2008 | Shu |
| 2008/0267916 A1 | 10/2008 | Gai et al. |
| 2008/0267917 A1 | 10/2008 | Niu et al. |
| 2008/0269228 A1 | 10/2008 | Moore et al. |
| 2008/0269502 A1 | 10/2008 | Gantz |
| 2008/0279821 A1 | 11/2008 | Niu et al. |
| 2008/0299075 A1 | 12/2008 | Bachand et al. |
| 2008/0311075 A1 | 12/2008 | Bachand et al. |
| 2008/0311077 A1 | 12/2008 | Chaudhary et al. |
| 2009/0004111 A1 | 1/2009 | Rice et al. |
| 2009/0005387 A1 | 1/2009 | Niu et al. |
| 2009/0035271 A1 | 2/2009 | Sun et al. |
| 2009/0036708 A1 | 2/2009 | Jia et al. |
| 2009/0041716 A1 | 2/2009 | Kim et al. |
| 2009/0041721 A1 | 2/2009 | Niu et al. |
| 2009/0043107 A1 | 2/2009 | Pack et al. |
| 2009/0047252 A1 | 2/2009 | Cai et al. |
| 2009/0068140 A1 | 3/2009 | Bachand et al. |
| 2009/0075869 A1 | 3/2009 | Holloway et al. |
| 2009/0093456 A1 | 4/2009 | Arnold et al. |
| 2009/0093533 A1 | 4/2009 | Beigelman et al. |
| 2009/0104151 A1 | 4/2009 | Hanson et al. |
| 2009/0105471 A1 | 4/2009 | Blatt et al. |
| 2009/0111757 A1 | 4/2009 | Lin et al. |
| 2009/0111969 A1 | 4/2009 | Blatt et al. |
| 2009/0111982 A1 | 4/2009 | Blatt et al. |
| 2009/0124808 A1 | 5/2009 | Busacca et al. |
| 2009/0130059 A1 | 5/2009 | Sun et al. |
| 2009/0148407 A1 | 6/2009 | Blatt et al. |
| 2009/0149491 A1 | 6/2009 | Liu et al. |
| 2009/0155209 A1 | 6/2009 | Blatt et al. |
| 2009/0162318 A1 | 6/2009 | Bender et al. |
| 2009/0163706 A1 | 6/2009 | Hildbrand et al. |
| 2009/0169510 A1 | 7/2009 | Blatt et al. |
| 2009/0175822 A1 | 7/2009 | Moore et al. |
| 2009/0176858 A1 | 7/2009 | Niu et al. |
| 2009/0180981 A1 | 7/2009 | Niu et al. |
| 2009/0186869 A1 | 7/2009 | Cottell et al. |
| 2009/0191153 A1 | 7/2009 | Sun et al. |
| 2009/0202478 A1 | 8/2009 | Bachand et al. |
| 2009/0202480 A1 | 8/2009 | Parsy et al. |
| 2009/0202483 A1 | 8/2009 | Bachand et al. |
| 2009/0257978 A1 | 10/2009 | Cho et al. |
| 2009/0269305 A1 | 10/2009 | Seiwert et al. |
| 2009/0274648 A1 | 11/2009 | Wang et al. |
| 2009/0274652 A1 | 11/2009 | Sin et al. |
| 2009/0281141 A1 | 11/2009 | Simmen et al. |
| 2009/0285773 A1 | 11/2009 | Sun et al. |
| 2009/0285774 A1 | 11/2009 | Sin et al. |
| 2009/0286814 A1 | 11/2009 | Lin et al. |
| 2009/0286843 A1 | 11/2009 | Blatt et al. |
| 2009/0297472 A1 | 12/2009 | Wang et al. |
| 2009/0304626 A1 | 12/2009 | Wang et al. |
| 2009/0304629 A1 | 12/2009 | Miao et al. |
| 2009/0306085 A1 | 12/2009 | Petter et al. |
| 2009/0326194 A1 | 12/2009 | Busacca et al. |
| 2010/0015092 A1 | 1/2010 | Nakajima et al. |
| 2010/0021540 A1 | 1/2010 | Gopinathan et al. |
| 2010/0022578 A1 | 1/2010 | Raboisson et al. |
| 2010/0028300 A1 | 2/2010 | Llinas-Brunet et al. |
| 2010/0029666 A1 | 2/2010 | Harper et al. |
| 2010/0036116 A1 | 2/2010 | Scalone et al. |
| 2010/0041591 A1 | 2/2010 | Niu et al. |
| 2010/0041728 A1 | 2/2010 | Antonov et al. |
| 2010/0055071 A1 | 3/2010 | Leivers et al. |
| 2010/0068176 A1 | 3/2010 | Belema et al. |
| 2010/0068182 A1 | 3/2010 | Huang et al. |
| 2010/0069294 A1 | 3/2010 | Petter et al. |
| 2010/0074890 A1 | 3/2010 | Hagel et al. |
| 2010/0080770 A1 | 4/2010 | Hiebert et al. |
| 2010/0080771 A1 | 4/2010 | Hiebert et al. |
| 2010/0080772 A1 | 4/2010 | Belema et al. |
| 2010/0081700 A1 | 4/2010 | Wang et al. |
| 2010/0081713 A1 | 4/2010 | Sharma et al. |
| 2010/0093792 A1 | 4/2010 | Berkenbusch et al. |
| 2010/0099695 A1 | 4/2010 | Liverton et al. |
| 2010/0113440 A1 | 5/2010 | Belfrage et al. |
| 2010/0124545 A1 | 5/2010 | Zhang et al. |
| 2010/0143499 A1 | 6/2010 | Condon |
| 2010/0144608 A1 | 6/2010 | Ku et al. |
| 2010/0150866 A1 | 6/2010 | Wang et al. |
| 2010/0158862 A1 | 6/2010 | Kim et al. |
| 2010/0160355 A1 | 6/2010 | Degoey et al. |
| 2010/0160403 A1 | 6/2010 | Link et al. |
| 2010/0168138 A1 | 7/2010 | Degoey et al. |
| 2010/0168384 A1 | 7/2010 | McDaniel et al. |
| 2010/0196321 A1 | 8/2010 | Cooper et al. |
| 2010/0215616 A1 | 8/2010 | Romine et al. |
| 2010/0215618 A1 | 8/2010 | Carter et al. |
| 2010/0221214 A1 | 9/2010 | Or et al. |
| 2010/0221215 A1 | 9/2010 | Qiu et al. |
| 2010/0221216 A1 | 9/2010 | Or et al. |

(56) References Cited

U.S. PATENT DOCUMENTS

| | | |
|---|---|---|
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0240698 A1 | 9/2010 | Simmen et al. |
| 2010/0249190 A1 | 9/2010 | Lopez et al. |
| 2010/0260708 A1 | 10/2010 | Belema et al. |
| 2010/0260710 A1 | 10/2010 | Parsy et al. |
| 2010/0260715 A1 | 10/2010 | Or et al. |
| 2010/0266543 A1 | 10/2010 | Qiu et al. |
| 2010/0267634 A1 | 10/2010 | Donner et al. |
| 2010/0272674 A1 | 10/2010 | Hiebert et al. |
| 2010/0292219 A1 | 11/2010 | Agarwal et al. |
| 2010/0297079 A1 | 11/2010 | Almond et al. |
| 2010/0303755 A1 | 12/2010 | Lopez et al. |
| 2010/0310512 A1 | 12/2010 | Guo et al. |
| 2010/0316607 A1 | 12/2010 | Or et al. |
| 2010/0317568 A1 | 12/2010 | Degoey et al. |
| 2011/0008288 A1 | 1/2011 | Or et al. |
| 2011/0020272 A1 | 1/2011 | Schubert |
| 2011/0059047 A1 | 3/2011 | Seiwert et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0065737 A1 | 3/2011 | Liu et al. |
| 2011/0070196 A1 | 3/2011 | Qiu et al. |
| 2011/0070197 A1 | 3/2011 | Or et al. |
| 2011/0077280 A1 | 3/2011 | Bender et al. |
| 2011/0092415 A1 | 4/2011 | Degoey et al. |
| 2011/0112100 A1 | 5/2011 | Milbank et al. |
| 2011/0136799 A1 | 6/2011 | Chern et al. |
| 2011/0142798 A1 | 6/2011 | Qiu et al. |
| 2011/0150827 A1 | 6/2011 | Dousson et al. |
| 2011/0152246 A1 | 6/2011 | Buckman et al. |
| 2011/0178107 A1 | 7/2011 | Wang et al. |
| 2011/0189129 A1 | 8/2011 | Qiu et al. |
| 2011/0195044 A1 | 8/2011 | Romine |
| 2011/0207660 A1 | 8/2011 | Sheth et al. |
| 2011/0207699 A1 | 8/2011 | Degoey et al. |
| 2011/0217261 A1 | 9/2011 | Or et al. |
| 2011/0218175 A1 | 9/2011 | Or et al. |
| 2011/0223134 A1 | 9/2011 | Nair et al. |
| 2011/0237579 A1 | 9/2011 | Li et al. |
| 2011/0237636 A1 | 9/2011 | Belema et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0294819 A1 | 12/2011 | Lopez et al. |
| 2011/0300104 A1 | 12/2011 | Qiu et al. |
| 2011/0312973 A1 | 12/2011 | Liepold et al. |
| 2012/0004196 A1 | 1/2012 | Degoey et al. |
| 2012/0028978 A1 | 2/2012 | Zhong et al. |
| 2012/0040977 A1 | 2/2012 | Li et al. |
| 2012/0076756 A1 | 3/2012 | Qiu et al. |
| 2012/0114600 A1 | 5/2012 | McKinnell et al. |
| 2012/0122864 A1 | 5/2012 | Zhong et al. |
| 2012/0172290 A1 | 7/2012 | Krueger et al. |
| 2012/0220562 A1 | 8/2012 | Degoey et al. |
| 2012/0258909 A1 | 10/2012 | Liepold et al. |
| 2013/0253008 A1 | 9/2013 | Ivachtchenko et al. |
| 2014/0024613 A1* | 1/2014 | Cohen et al. .......... 514/49 |
| 2014/0080886 A1* | 3/2014 | Pilot-Matias et al. ........ 514/422 |
| 2014/0323395 A1* | 10/2014 | Bernstein et al. ............. 514/4.3 |
| 2015/0011481 A1* | 1/2015 | Vilchez et al. ............. 514/21.1 |
| 2015/0024999 A1* | 1/2015 | Awni et al. .................. 514/4.3 |
| 2017/0368066 A1 | 12/2017 | Miller et al. |

FOREIGN PATENT DOCUMENTS

| | | |
|---|---|---|
| DE | 4442257 A1 | 5/1996 |
| EP | 1437362 A1 | 7/2004 |
| EP | 1169339 B1 | 9/2004 |
| EP | 1880715 A1 | 1/2008 |
| EP | 1472278 B1 | 11/2008 |
| EP | 1455809 B1 | 6/2011 |
| EP | 2583680 A2 | 4/2013 |
| EP | 2242751 B1 | 7/2015 |
| JP | 2003282270 A | 10/2003 |
| JP | 2007320925 A | 12/2007 |
| JP | 2010126571 A | 6/2010 |
| RU | 2286343 C2 | 10/2006 |
| WO | 9427627 A1 | 12/1994 |
| WO | 9640751 A1 | 12/1996 |
| WO | 9640752 A1 | 12/1996 |
| WO | 9907733 A2 | 2/1999 |
| WO | 9961020 A1 | 12/1999 |
| WO | 0000179 A1 | 1/2000 |
| WO | 0009543 A2 | 2/2000 |
| WO | 0009558 A1 | 2/2000 |
| WO | 0012521 A1 | 3/2000 |
| WO | 0059929 A1 | 10/2000 |
| WO | 0214314 A2 | 2/2002 |
| WO | 02060926 A2 | 8/2002 |
| WO | 03053349 A2 | 7/2003 |
| WO | 03064416 A1 | 8/2003 |
| WO | 03064455 A2 | 8/2003 |
| WO | 03064456 A1 | 8/2003 |
| WO | 03066103 A1 | 8/2003 |
| WO | 03082186 A2 | 10/2003 |
| WO | 03099274 A1 | 12/2003 |
| WO | 2004005283 A1 | 1/2004 |
| WO | 2004014313 A2 | 2/2004 |
| WO | 2004014852 A2 | 2/2004 |
| WO | 2004030670 A1 | 4/2004 |
| WO | 2004037855 A1 | 5/2004 |
| WO | 2004039833 A1 | 5/2004 |
| WO | 2004072243 A2 | 8/2004 |
| WO | 2004087741 A1 | 10/2004 |
| WO | 2004089974 A1 | 10/2004 |
| WO | 2004092203 A2 | 10/2004 |
| WO | 2004093798 A2 | 11/2004 |
| WO | 2004093915 A1 | 11/2004 |
| WO | 2004094452 A2 | 11/2004 |
| WO | 2004103996 A1 | 12/2004 |
| WO | 2005028501 A1 | 3/2005 |
| WO | 2005037214 A2 | 4/2005 |
| WO | 2005046712 A1 | 5/2005 |
| WO | 2005051410 A1 | 6/2005 |
| WO | 2005051980 A1 | 6/2005 |
| WO | 2005054430 A2 | 6/2005 |
| WO | 2005070955 A1 | 8/2005 |
| WO | 2005075502 A1 | 8/2005 |
| WO | 2005090383 A2 | 9/2005 |
| WO | 2005095403 A2 | 10/2005 |
| WO | 2005116054 A1 | 12/2005 |
| WO | 2006000085 A1 | 1/2006 |
| WO | 2006005479 A2 | 1/2006 |
| WO | 2006020276 A2 | 2/2006 |
| WO | 2006020951 A1 | 2/2006 |
| WO | 2006033703 A1 | 3/2006 |
| WO | 2006033851 A1 | 3/2006 |
| WO | 2006033878 A1 | 3/2006 |
| WO | 2006036614 A2 | 4/2006 |
| WO | 2006093867 A1 | 9/2006 |
| WO | 2006096652 A2 | 9/2006 |
| WO | 2006114405 A2 | 11/2006 |
| WO | 2006119061 A2 | 11/2006 |
| WO | 2006122188 A2 | 11/2006 |
| WO | 2006128455 A2 | 12/2006 |
| WO | 2006130552 A2 | 12/2006 |
| WO | 2006130553 A2 | 12/2006 |
| WO | 2006130607 A2 | 12/2006 |
| WO | 2006130626 A2 | 12/2006 |
| WO | 2006130627 A2 | 12/2006 |
| WO | 2006130628 A2 | 12/2006 |
| WO | 2006130666 A2 | 12/2006 |
| WO | 2006130686 A2 | 12/2006 |
| WO | 2006130687 A2 | 12/2006 |
| WO | 2006130688 A2 | 12/2006 |
| WO | 2006133326 A1 | 12/2006 |
| WO | 2007001406 A2 | 1/2007 |
| WO | 2007005838 A2 | 1/2007 |
| WO | 2007008657 A2 | 1/2007 |

(56) References Cited

FOREIGN PATENT DOCUMENTS

| | | |
|---|---|---|
| WO | 2007009109 A2 | 1/2007 |
| WO | 2007009227 A1 | 1/2007 |
| WO | 2007014919 A1 | 2/2007 |
| WO | 2007014921 A1 | 2/2007 |
| WO | 2007014923 A1 | 2/2007 |
| WO | 2007014924 A1 | 2/2007 |
| WO | 2007014925 A1 | 2/2007 |
| WO | 2007014926 A1 | 2/2007 |
| WO | 2007015824 A2 | 2/2007 |
| WO | 2007016441 A1 | 2/2007 |
| WO | 2007021494 A2 | 2/2007 |
| WO | 2007030656 A1 | 3/2007 |
| WO | 2007041713 A1 | 4/2007 |
| WO | 2007044893 A2 | 4/2007 |
| WO | 2007044933 A1 | 4/2007 |
| WO | 2007056120 A1 | 5/2007 |
| WO | 2007070556 A2 | 6/2007 |
| WO | 2007070600 A2 | 6/2007 |
| WO | 2007076034 A2 | 7/2007 |
| WO | 2007076035 A2 | 7/2007 |
| WO | 2007081517 A2 | 7/2007 |
| WO | 2007082554 A1 | 7/2007 |
| WO | 2007131366 A1 | 11/2007 |
| WO | 2007131966 A1 | 11/2007 |
| WO | 2007139585 A1 | 12/2007 |
| WO | 2007143694 A2 | 12/2007 |
| WO | 2007144174 A1 | 12/2007 |
| WO | 2007148135 A1 | 12/2007 |
| WO | 2008002924 A2 | 1/2008 |
| WO | 2008008502 A1 | 1/2008 |
| WO | 2008008776 A2 | 1/2008 |
| WO | 2008014236 A1 | 1/2008 |
| WO | 2008014238 A2 | 1/2008 |
| WO | 2008019289 A2 | 2/2008 |
| WO | 2008019303 A2 | 2/2008 |
| WO | 2008021927 A2 | 2/2008 |
| WO | 2008021928 A2 | 2/2008 |
| WO | 2008021936 A2 | 2/2008 |
| WO | 2008021956 A2 | 2/2008 |
| WO | 2008021960 A2 | 2/2008 |
| WO | 2008022006 A2 | 2/2008 |
| WO | 2008039538 A2 | 4/2008 |
| WO | 2008046860 A2 | 4/2008 |
| WO | 2008051475 A2 | 5/2008 |
| WO | 2008051514 A2 | 5/2008 |
| WO | 2008057208 A2 | 5/2008 |
| WO | 2008057209 A2 | 5/2008 |
| WO | 2008057871 A2 | 5/2008 |
| WO | 2008057873 A2 | 5/2008 |
| WO | 2008057875 A2 | 5/2008 |
| WO | 2008057995 A2 | 5/2008 |
| WO | 2008059046 A1 | 5/2008 |
| WO | 2008060927 A2 | 5/2008 |
| WO | 2008062457 A2 | 5/2008 |
| WO | 2008064057 A1 | 5/2008 |
| WO | 2008064061 A1 | 5/2008 |
| WO | 2008064066 A1 | 5/2008 |
| WO | 2008064218 A2 | 5/2008 |
| WO | 2008070447 A2 | 6/2008 |
| WO | 2008070733 A2 | 6/2008 |
| WO | 2008074450 A2 | 6/2008 |
| WO | 2008086161 A1 | 7/2008 |
| WO | 2008092954 A2 | 8/2008 |
| WO | 2008095058 A1 | 8/2008 |
| WO | 2008096001 A1 | 8/2008 |
| WO | 2008098368 A1 | 8/2008 |
| WO | 2008101665 A1 | 8/2008 |
| WO | 2008106130 A2 | 9/2008 |
| WO | 2008114006 A1 | 9/2008 |
| WO | 2008124384 A2 | 10/2008 |
| WO | 2008128121 A1 | 10/2008 |
| WO | 2008128921 A1 | 10/2008 |
| WO | 2008133753 A2 | 11/2008 |
| WO | 2008137779 A2 | 11/2008 |
| WO | 2008141227 A1 | 11/2008 |
| WO | 2008144380 A1 | 11/2008 |
| WO | 2009003009 A1 | 12/2008 |
| WO | 2009005676 A2 | 1/2009 |
| WO | 2009005677 A1 | 1/2009 |
| WO | 2009010804 A1 | 1/2009 |
| WO | 2009014730 A1 | 1/2009 |
| WO | 2009020534 A2 | 2/2009 |
| WO | 2009020825 A1 | 2/2009 |
| WO | 2009020828 A1 | 2/2009 |
| WO | 2009039127 A1 | 3/2009 |
| WO | 2009039134 A1 | 3/2009 |
| WO | 2009053828 A2 | 4/2009 |
| WO | 2009067108 A1 | 5/2009 |
| WO | 2009070689 A1 | 6/2009 |
| WO | 2009070692 A1 | 6/2009 |
| WO | 2009073713 A1 | 6/2009 |
| WO | 2009073719 A1 | 6/2009 |
| WO | 2009073780 A1 | 6/2009 |
| WO | 2009080542 A1 | 7/2009 |
| WO | 2009082697 A1 | 7/2009 |
| WO | 2009082701 A1 | 7/2009 |
| WO | 2009085659 A1 | 7/2009 |
| WO | 2009094224 A1 | 7/2009 |
| WO | 2009099596 A2 | 8/2009 |
| WO | 2009102318 A1 | 8/2009 |
| WO | 2009102325 A1 | 8/2009 |
| WO | 2009102568 A1 | 8/2009 |
| WO | 2009102633 A1 | 8/2009 |
| WO | 2009102694 A1 | 8/2009 |
| WO | 2009129109 A1 | 10/2009 |
| WO | 2009/139792 | 11/2009 |
| WO | 2009136290 A1 | 11/2009 |
| WO | 2009137432 A1 | 11/2009 |
| WO | 2009140475 A1 | 11/2009 |
| WO | 2009140500 A1 | 11/2009 |
| WO | 2009142842 A2 | 11/2009 |
| WO | 2009143361 A1 | 11/2009 |
| WO | 2009146347 A1 | 12/2009 |
| WO | 2009148923 A1 | 12/2009 |
| WO | 2009149377 A1 | 12/2009 |
| WO | 2009155709 A1 | 12/2009 |
| WO | 2010000459 A1 | 1/2010 |
| WO | 2010015090 A1 | 2/2010 |
| WO | 2010015545 A1 | 2/2010 |
| WO | 2010017035 A2 | 2/2010 |
| WO | 2010017401 A1 | 2/2010 |
| WO | 2010021717 A2 | 2/2010 |
| WO | 2010028236 A1 | 3/2010 |
| WO | 2010030359 A2 | 3/2010 |
| WO | 2010033443 A1 | 3/2010 |
| WO | 2010033444 A1 | 3/2010 |
| WO | 2010033466 A1 | 3/2010 |
| WO | 2010034105 A1 | 4/2010 |
| WO | 2010036551 A1 | 4/2010 |
| WO | 2010036871 A1 | 4/2010 |
| WO | 2010036896 A1 | 4/2010 |
| WO | 2010039793 A1 | 4/2010 |
| WO | 2010042834 A1 | 4/2010 |
| WO | 2010048468 A1 | 4/2010 |
| WO | 2010059667 A1 | 5/2010 |
| WO | 2010059858 A1 | 5/2010 |
| WO | 2010059937 A1 | 5/2010 |
| WO | 2010062821 A1 | 6/2010 |
| WO | 2010065577 A1 | 6/2010 |
| WO | 2010065668 A1 | 6/2010 |
| WO | 2010065674 A1 | 6/2010 |
| WO | 2010065681 A1 | 6/2010 |
| WO | 2010075376 A2 | 7/2010 |
| WO | 2010075380 A1 | 7/2010 |
| WO | 2010077783 A1 | 7/2010 |
| WO | 2010080389 A1 | 7/2010 |
| WO | 2010088394 A1 | 8/2010 |
| WO | 2010091413 A1 | 8/2010 |
| WO | 2010096302 A1 | 8/2010 |
| WO | 2010096462 A1 | 8/2010 |
| WO | 2010096777 A1 | 8/2010 |
| WO | 2010099527 A1 | 9/2010 |
| WO | 2010111483 A1 | 9/2010 |
| WO | 2010111534 A1 | 9/2010 |

(56) References Cited

FOREIGN PATENT DOCUMENTS

| | | |
|---|---|---|
| WO | 2010111673 A1 | 9/2010 |
| WO | 2010115767 A1 | 10/2010 |
| WO | 2010117635 A1 | 10/2010 |
| WO | 2010117704 A1 | 10/2010 |
| WO | 2010117977 A1 | 10/2010 |
| WO | 2010118078 A1 | 10/2010 |
| WO | 2010120476 A2 | 10/2010 |
| WO | 2010120621 A1 | 10/2010 |
| WO | 2010120935 A1 | 10/2010 |
| WO | 2010122162 A1 | 10/2010 |
| WO | 2010128521 A2 | 11/2010 |
| WO | 2010132538 A1 | 11/2010 |
| WO | 2010132601 A1 | 11/2010 |
| WO | 2010135520 A1 | 11/2010 |
| WO | 2010135748 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |
| WO | 2010144646 A2 | 12/2010 |
| WO | 2010148006 A1 | 12/2010 |
| WO | 2011004276 A1 | 1/2011 |
| WO | 2011009084 A2 | 1/2011 |
| WO | 2011015658 A1 | 2/2011 |
| WO | 2011017389 A1 | 2/2011 |
| WO | 2011026920 A1 | 3/2011 |
| WO | 2011028596 A1 | 3/2011 |
| WO | 2011031904 A1 | 3/2011 |
| WO | 2011031934 A1 | 3/2011 |
| WO | 2011050146 A1 | 4/2011 |
| WO | 2011054834 A1 | 5/2011 |
| WO | 2011059850 A1 | 5/2011 |
| WO | 2011059887 A1 | 5/2011 |
| WO | 2011060000 A1 | 5/2011 |
| WO | 2011063501 A1 | 6/2011 |
| WO | 2011063502 A1 | 6/2011 |
| WO | 2011066241 A1 | 6/2011 |
| WO | 2011068941 A2 | 6/2011 |
| WO | 2011075439 A1 | 6/2011 |
| WO | 2011075607 A1 | 6/2011 |
| WO | 2011075615 A1 | 6/2011 |
| WO | 2011079327 A1 | 6/2011 |
| WO | 2011081918 A1 | 7/2011 |
| WO | 2011082077 A1 | 7/2011 |
| WO | 2011087740 A1 | 7/2011 |
| WO | 2011091417 A1 | 7/2011 |
| WO | 2011091446 A1 | 7/2011 |
| WO | 2011091532 A1 | 8/2011 |
| WO | 2011109274 A1 | 9/2011 |
| WO | 2011112429 A1 | 9/2011 |
| WO | 2011112558 A2 | 9/2011 |
| WO | 2011119853 A1 | 9/2011 |
| WO | 2011119858 A1 | 9/2011 |
| WO | 2011119860 A1 | 9/2011 |
| WO | 2011119870 A1 | 9/2011 |
| WO | 2011127350 A1 | 10/2011 |
| WO | 2011146401 A1 | 11/2011 |
| WO | 2011/156578 | 12/2011 |
| WO | 2011150243 A1 | 12/2011 |
| WO | 2011156543 A2 | 12/2011 |
| WO | 2011156578 A1 | 12/2011 |
| WO | 2012039717 A1 | 3/2012 |
| WO | 2012040389 A2 | 3/2012 |
| WO | 2012040923 A1 | 4/2012 |
| WO | 2012040924 A1 | 4/2012 |
| WO | 2012041014 A1 | 4/2012 |
| WO | 2012041227 A1 | 4/2012 |
| WO | 2012050848 A1 | 4/2012 |
| WO | 2012050850 A1 | 4/2012 |
| WO | 2012051361 A1 | 4/2012 |
| WO | 2012068234 A2 | 5/2012 |
| WO | 2012074437 A2 | 6/2012 |
| WO | 2012083043 A1 | 6/2012 |
| WO | 2012083048 A2 | 6/2012 |
| WO | 2012083053 A2 | 6/2012 |
| WO | 2012083058 A2 | 6/2012 |
| WO | 2012083059 A1 | 6/2012 |
| WO | 2012083061 A2 | 6/2012 |
| WO | 2012083164 A1 | 6/2012 |
| WO | 2012087976 A2 | 6/2012 |
| WO | 2012116257 A1 | 8/2012 |
| WO | 2014004674 A2 | 1/2014 |
| WO | 2014063101 A1 | 4/2014 |

OTHER PUBLICATIONS

Ohno et al., J. Clin. Microbiol. 35:201-207 (1997).*
Thompson, JR, World J. Gastroenterology 20:7079-7088 (2014).*
U.S. Appl. No. 12/941,352, filed Nov. 2010, Collins et al.*
U.S. Appl. No. 13/113,452, filed May 2011, Collins et al.*
U.S. Appl. No. 13/474,398, filed May 2012, Collins et al.*
U.S. Appl. No. 14/048,995, filed Oct. 2013, Bernstein et al.*
U.S. Appl. No. 14/208,266, filed Mar. 2014, Cohen et al.*
U.S. Appl. No. 14/536,894, filed Nov. 2014, Cohen et al.*
U.S. Appl. No. 14/557,524, filed Dec. 2014, Bernstein et al.*
U.S. Appl. No. 14/606,369, filed Jan. 2015, Awni et al.*
U.S. Appl. No. 14/628,849, filed Feb. 2015, Awni et al.*
U.S. Appl. No. 14/670,734, filed Mar. 2015, Awni et al.*
Greco W.R., et al., "The Search for Synergy: A Critical Review from a Response Surface Perspective," Pharmacological Reviews, 1995, vol. 47 (2), pp. 331-385.
Lohmann V., et al., "Replication of Subgenomic Hepatitis C Virus RNAs in a Hepatoma Cell Line," Science, 1999, vol. 285 (5424), pp. 110-113.
Prichard M.N., et al., "A Three-Dimensional Model to Analyze Drug-Drug Interactions," Antiviral Research, 1990, vol. 14 (4-5), pp. 181-206.
SAS 9.1 SQL Procedure User's Guide, 2004, 166 pages.
International Search Report for Application No. PCT/US2011/065468, mailed on Mar. 26, 2012, 3 pages.
Rosenberg et al., "Amorphous embedding of a lipophilic drug substance by meltrex-technology," Journal of Controlled Release. Abstracts 2003, vol. 87, pp. 264-267.
L-selectride, Retrieved from the Internet<URL: http://en.wikipedia.org/w/index.php"oldid=488453454>, downloaded Apr. 2012.
Antares Health Products, "Vitamin E TPGS" downloaded from http://www.tpgs.com/, downloaded Jan. 31, 2013.
International Search Report for Application No. PCT/US2011/065486, mailed on Mar. 26, 2012, 3 pages.
Abagyan R. et al., "ICM-A New Method for Protein Modeling and Design: Applications to Docking and Structure Prediction from the Distorted Native Conformation," Journal of Computational Chemistry, 1994, vol. 15 (5), pp. 488-506.
Adjabeng G. et al., "Novel Class of Tertiary Phosphine Ligands Based on a Phospha-adamantane Framework and use in the Suzuki cross-Coupling Reactions of Aryl Halides Under Mild Conditions," Organic Letters, 2003, vol. 5 (6), pp. 953-955.
Adjabeng G. et al., "Palladium Complexes of 1,3,5,7-tetramethyl-2,4,8-trioxa-6-phenyl-6-phosphaadamantane. Synthesis, Crystal Structure and Use in the Suzuki and Sonogashira Reactions and the Alpha-arylation of Ketones," The Journal of Organic Chemistry, 2004, vol. 69 (15), pp. 5082-5086.
Akimoto M. et al., "Gastric pH Profiles of Beagle Dogs and their Use as an Alternative to Human Testing," European Journal of Pharmaceutics and Biopharmaceutics, 2000, vol. 49 (2), pp. 99-102.
Aldous D.J. et al., "A Simple Enantioselective Preparation of (2S,5S)-2,5-diphenylpyrrolidine and Related Diaryl Amines," Tetrahedron Asymmetry, 2000, vol. 11, pp. 2455-2462.
Alesso E.N. et al., "Synthesis of Diastereoisomeric 1,2,3-Triphenylindans," Australian Journal of Chemistry, 1997, vol. 50, pp. 149-152.
Alonzo D E et al., "Understanding the Behavior of Amorphous Pharmaceutical Systems During Dissolution," Pharmaceutical Research, 2010, vol. 27 (4), pp. 608-618.
Altschuel S.F. et al., "Basic Local Alignment Search Tool," Journal of Molecular Biology, 1990, 215 (3), pp. 403-410.

(56) References Cited

OTHER PUBLICATIONS

Altschul S.F. et al., "Gapped BLAST and PSI-BLAST: A New Generation of Protein Database Search Programs," Nucleic Acids Research, 1997, 25 (17), pp. 3389-3402.
Angiolini M. et al., "Synthesis of Azabicycloalkane Amino Acid Scaffolds as Reverse-Turn Inducer Dipeptide Mimics," European Journal Organization Chemistry, 2000, vol. 2000 (14), pp. 2571-2581.
Baker D. et al., "Protein Structure Prediction and Structural Genomics," Science, 2001, vol. 294 (5540), pp. 93-96.
Barbato G. et al , "Inhibitor Binding Induces Active Site Stabilization of the Hcv Ns3 Protein Serine Protease Domain," The EMBO Journal, 2000, vol. 19 (6), pp. 1195-1206.
Bartenschlager R., "Hepatitis C Virus Molecular Clones: From cDNA to Infectious Virus Particles in Cell Culture," Current Opinion in Microbiology, 2006, vol. 9 (4), pp. 416-422.
Bartenschlager R., "Hepatitis C Virus Replicons: Potential Role for Drug Development," Nature Reviews Drug Discovery, 2002, vol. 1 (11), pp. 911-916.
Bauer H. et al., "Methods for Determining Wetability and Their Potential Uses in Pharmaceutical Technology", Pharmacy, 1975, 30 (11), 689-693 (with Translation).
Beaumont, K. et al., "Design of Ester Prodrugs to Enhance Oral Absorption of Poorly Permeable Compounds Challenges to the Discovery Scientist," Current Drug Metabolism, 2003, vol. 4 (6), pp. 461-485.
Boehm T. et al., "Uber Die Bildung Von Gamma-Piperidonderivaten Aus Azetessigester, Aromatischen Aldehyden and Aminen, Eine Modifikation Der Hantzschschen Pyridinsynthese," Pharmaceutical, 1943, vol. 281, pp. 62-77 (with translation).
Bohm H.J., "The Computer Program LUDI: A New Method for the De Novo Design of Enzyme Inhibitors," Journal of Computer-Aided Molecular Design, 1992, vol. 6, pp. 61-78.
Brandrup J. et al., Editors, Polymer Handbook, Second Ed., Wiley-lnterscience Publishers, 1975, Table of Contents.
Brelienbach J. et al., "Confocal Raman-Spectroscopy: Analytical Approach to Solid Dispersions and Mapping of Drugs," 1999, Pharmaceutical Research, vol. 16 (7), pp. 1109-1113.
Brettle R. et al., "A Highly Efficient Enzymic Route to Novel Chiral Liquid Crystals based on 3-Aryl-2-cycloalken-1-ones," Journal of the Chemical Society, Chemical Communications, 1994, vol. 1994 (19), pp. 2305-2306.
Brunger A.T. et al., "Recent Developments for the Efficient Crystallographic Refinement of Macromolecular Structures," Current Opinion in Structural Biology, 1998, vol. 8, pp. 606-611.
Buhler, V. "KOLLIDON®: Polyvinylpyrrolidone Excipients for the Pharmaceutical Industry," BASF SE, Pharma Ingredients & Services, Ludwlgshafen, Germany, Mar. 2008, 9th Ed. (331 pages).
Buhler, V., "Polyvinylpyrrolidone-Excipients for Pharmaceuticals" Povidone, Crospovidone and CopovidoneSpringer, Published 2005 (258 pages), Submitted in nine parts due to size.
Bundgaard H. Editor "Design of Pro Drugs," 1985 Elsevier Science Publishers, Chapters 1 and 2, pp. 1-133.
Charifson P.S. et al., "Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Stucture-Activity Relationships," Journal of Medicinal Chemistry, 2008, vol. 51 (17), pp. 5243-5263.
Chong J.M. et al., "Asymmetric Synthesis of trans.2,5-Diphenylpyrrolidine: A C2-Symmetric Chiral Amine," Tetrahedron Asymmetry, 1995, vol. 6 (2), pp. 409-418.
Clark W.M. et al., "A Highly Enantioselective Conjugate Reduction of 3-Arylinden-l-ones Using Bakers' Yeast for the Preparation of (S)-3-Arylindan-l-ones," Organic Letters, 1999, vol. 1 (1), pp. 1839-1842.
Clarke P.A. et al., "Pot, Atom and Step Economic (PASE) Synthesis of Highly Functionalized Piperidines: A Five-Component Condensation," Tetrahedron Letters, 2007, vol. 48, pp. 5209-5212.

Clarke P.A. et al., "Pot, Atom and Step Economic (PASE) Synthesis of Highly Substituted Piperidines:A Five-Component Condensation," Synthesis, 2008, No. 21, pp. 3530-3532.
Collado I. et al., "Stereoselective Addition of Grignard-Derived Organocopper Reagents to N-Acyliminium Ions: Synthesis of Enantiopure 5- and 4,5-Substituted Prolinates ," Journal of Organic Chemistry, 1995, vol. 60, pp. 5011-5015.
Conte I. et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19 (6), pp. 1779-1783.
Cornell, W.D. et al., "A Second Generation Force Field for the Simulation of Proteins, Nucleic Acids, and Organic Molecules," Journal of the American Chemical Society, 1995, vol. 117, pp. 5179-5197.
De Francesco R. et al., "Challenges and Successes in Developing New Therapies for Hepatitis C," Nature, 2005, vol. 436 (7053), pp. 953-960.
Dell'Erba C. et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-Endo-Trig Cyclization," European Journal of Organic Chemistry, 2000, pp. 903-912.
Dymock B.W., "Emerging Therapies for Hepatitis C Virus Infection," Expert Opinion on Emerging Drugs, 2001, vol. 6 (1), pp. 13-42.
Effenberger F. et al., "Synthesis, Structure, and Spectral Behavior of Donor-Acceptor Substituted Biphenyls," The Journal of Organic Chemistry, 1983, vol. 48 (24), pp. 4649-4658.
Eldridge M.D. et al., "Empirical Scoring Functions: I. The Development of a Fast Empirical Scoring Function to Estimate the Binding Affinity of Ligands in Receptor Complexes," Journal of Computer Aided Molecular Design, 1997, vol. 11 (5), pp. 425-445.
Eswar N. et al., "Comparative Protein Structure Modeling Using Modeller," Current Protocols in Bioinformatics, 2006, Suppl. 15, pp. 5.6.1-5.6.30.
Ettmayer P. et al., "Lessons Learned from Marketed and Investigational Prodrugs," Journal Medicinal Chemistry, 2004, vol. 47 (10), pp. 2393-2404.
European Search Report for Application No. EP12155991, dated Mar. 29, 2012, 2 pages.
Fan X. et al., "An Efficient and Practical Synthesis of the HIV Protease Inhibitor Atazanavir via a Highly Diastereoselective Reduction Approach," Organic Process Research and Development, 2008, vol. 12 (1), pp. 69-75.
Feig M. et al., "Performance Comparison of Generalized Born and Poisson Methods in the Calculation of Electrostatic Salvation Energies for Protein Structures," Journal of Computational Chemistry, 2004, vol. 25 (2), pp. 265-284.
Fiedler, H. P., Encyclopedia of Excipients for Pharmaceuticals, Cosmetics and related Areas, 5th Edition, Editio Cantor Verlag Aulendorf, 2002, Table of Contents (6 pages).
Fiser A. et al., "Modeling of Loops in Protein Structures," Protein Science, 2000, vol. 9 (9), pp. 1753-1773.
Forster A. et al., "Selection of Excipients for Melt Extrusion with Two Poorly Water-Soluble Drugs by Solubility Parameter Calculation and Thermal Analysis," International Journal of Pharmaceutics, 2001, vol. 226, pp. 147-161.
Galun E. et al., "Hepatitis C Virus Viremia in SCID-BNX Mouse Chimera," Journal of Infectious Diseases, 1995, vol. 172 (1), pp. 25-30.
Gastreich M. et al., "Ultrafast De Novo Docking Combining Pharmacophores and Combinatorics," Journal of Computer-Aided Molecular Design, 2006, vol. 20 (12), pp. 717-734.
Gillet V. et al., "SPROUT: A Program for Structure Generation," Journal of Computer-Aided Molecular Design, 1993, vol. 7 (2), pp. 127-153.
Gohlke H. et al., "Approaches to the Description and Prediction of the Binding Affinity of Small-Molecule Ligands to Macromolecular Receptors," Angewandte Chemie International Edition, 2002, vol. 41 (15), pp. 2644-2676.

(56) References Cited

OTHER PUBLICATIONS

Goodford P.J., "A Computational Procedure for Determining Energetically Favorable Binding Sites on Biologically Important Macromolecules," Journal of Medicinal Chemistry, 1985, vol. 28 (7), pp. 849-857.
Goodsell D.S. et al., "Automated Docking of Substrates to Proteins by Simulated Annealing," Proteins, 1990, vol. 8 (3), pp. 195-202.
Gordon T.D., et al, "Synthetic Approaches to the Azole Peptide Mimetics," Tetrahedron Letters, 1993, vol. 34(12), pp. 1901-1904.
Goudreau N. et al., "NMR Structural Characterization of Peptide Inhibitors Bound to the Hepatitis C Virus NS3 Protease: Design of a New P2 Substituent," Journal of Medicinal Chemistry, 2004, vol. 47 (1), pp. 123-132.
Goudreau N. et al., "The therapeutic potential of NS3 protease inhibitors in HCV infection," Expert Opinion on Investigational Drugs, vol. 14, No. 9, 2005, 1129-1144.
Greene, T.W. et al., Protective Groups in Organic Synthesis, 3rd Edition, John Wiley and Sons, Inc., 1999, Table of Contents, Abbreviations, pp. 494-653 and Index (pp. 749-779).
Halperin I. et al., "Principles of Docking: An Overview of Search Algorithms and a Guide to Scoring Functions," Proteins: Structure, Function, and Genetics, 2002, vol. 47 (4), pp. 409-443.
Han H.K. et al., "Targeted Prodrug Design to Optimize Drug Delivery," AAPS PharmSci, 2000, vol. 2 (1), pp. 1-11.
Hartwig J.F. et al., "111.3.2 Palladium-Catalyzed Amination of Aryl Halides and Related Reactions," Handbook of Organopalladium Chemistry for Organic Synthesis, E-I Negishi Editor, John Wiley & Sons, Inc. 2002, pp. 1051-1096.
Hoover J. et al. Editors, Remington's Pharmaceutical Sciences, 15th Edition, 1975, Table of Contents.
Hubbard S.R. et al., "Src Autoinhibition: Let us Count the Ways," Nature Structural Biology, 1999, vol. 6 (8), pp. 711-714.
International Search Report and Written Opinion for Application No. PCT/US2010/038077, mailed Jan. 21, 2011, 16 pages.
International Search Report for Application No. PCT/US2009/05082, mailed on Apr. 1, 2010, 1 page.
International Search Report and Written Opinion for Application No. PCT/US2009/069177, mailed on Aug. 10, 2010, 17 pages.
International Preliminary Report on Patentability and Written Opinion for Application No. PCT/US2009/069188, mailed on Jun. 29, 2011, 10 pages.
International Search Report for Application No. PCT/US2009/069188, mailed on Jun. 8, 2010, 4 pages.
International Preliminary Report on Patentability and Written Opinion for Application No. PCT/US2010/031102, mailed on Oct. 18, 2011, 7 pages.
International Search Report for Application No. PCT/US2010/031102, mailed on Sep. 1, 2010, 4 pages.
International Search Report for Application No. PCT/US2011/027511, mailed on Nov. 10, 2011, 3 pages.
International Search Report for Application No. PCT/US2011/039769, mailed on Oct. 6, 2011, 4 pages.
International Search Report for Application No. PCT/US2011/056045, mailed on Apr. 2, 2012, 4 pages.
International Search Report for Application No. PCT/US2011/065206, mailed on May 22, 2012, 3 pages.
International Search Report for Application No. PCT/US2011/065215, mailed on Jun. 12, 2012, 3 pages.
International Search Report for Application No. PCT/US2011/065224, mailed on Jun. 12, 2012, 3 pages.
International Search Report for Application No. PCT/US2011/065239, mailed on Jul. 30, 2012, 3 pages.
International Search Report for Application No. PCT/US2011/065242, mailed on May 22, 2012, 3 pages.
International Search Report for Application No. PCT/US2011/065247, mailed on Jun. 12, 2012, 3 pages.
International Search Report for Application No. PCT/US2012/026456, mailed on Jun. 22, 2012, 3 pages.
International Search Report and Written Opinion for Application No. PCT/US2013/065760, mailed Dec. 12, 2013, 13 pages.
Jacques et al., "Enantiomers, Racemates, and Resolutions," J. Wiley & Sons, 1981 Chapter 3, pp. 197-213.
Jeffrey J.L. et al., "Concise Synthesis of Pauciflorol F Using a Larock Annulation," Organic Letters, 2009, vol. 11 (23), pp. 5450-5453.
Jing Q. et al., "Bulky Achiral Trimylphosphines Mimic BINAP in Ru(11)-Catalyzed Asymmetric Hydrogenation of Ketones," Advanced Synthesis & Catalysis, 2005, vol. 347, pp. 1193-1197.
Johansson A. et al., "Acyl Sulfonamides as Potent Protease Inhibitors of the Hepatitis C Virus Full-Length NS3 (Protease-Helicase/NTPase): A Comparative Study of Different C-Terminals," Bioorganic & Medicinal Chemistry, 2003, vol. 11 (12), pp. 2551-2568.
Jones G. et al., "Development and Validation of a Genetic Algorithm for Flexible Docking," Journal of Molecular Biology, 1997, vol. 267 (3), pp. 727-748.
Jones G. et al., "Docking Small-Molecule Ligands into Active Sites," Current Opinion in Biotechnology, 1995, vol. 6 (6), pp. 652-656.
Jones G. et al., "Molecular Recognition of Receptor Sites using a Genetic Algorithm with a Description of Desolvation," Journal of Molecular Biology, 1995, vol. 245 (1), pp. 43-53.
Kahlson G. et al., "Mobilization and Formation of Histamine in the Gastric Mucosa as Related to Acid Secretion," Journal of Physiology, 1964, vol. 174, pp. 400-416.
Khan A.T. et al., "Effects of Substituents in the β-Position of 1,3-Dicarbonyl Compounds in Bromodimethylsulfonium Bromide-Catalyzed Multicomponent Reactions: A Facile Access to Functionalized Piperidines," Journal of Organic Chemistry, 2008, vol. 73, pp. 8398-8402.
Kim J.L. et al., "Crystal Structure of the Hepatitis C Virus NS3 Protease Domain Complexed with a Synthetic NS4A Cofactor Peptide," Cell, 1996, vol. 87 (2), pp. 343-355.
KOLLIDON® VA 64 and KOLLIDON® VA 64 Fine, Technical Information, BASF Chemical Company, Pharma Ingredients & Services, Aug. 2011 Issue (16 pages).
Kolykhalov A.A. et al., "Transmission of Hepatitis C by Intrahepatic Inoculation with Transcribed RNA," Science, 1997, vol. 277 (5325), pp. 570-574.
Kuethe J.T. et al., "Asymmetric Synthesis of 1,2,3-Trisubstituted Cyclopentanes and Cyclohexanes as Kev Components of Substance P Antagonists," Journal of Organic Chemistry, 2002, vol. 67 (17), pp. 5993-6000.
Kuntz I.D. et al., "A Geometric Approach to Macromolecule-Ligand Interactions," Journal of Molecular Biology, 1982, vol. 161 (2), pp. 269-288.
Lattman, E., "Use of the Rotation and Translation Functions," Methods in Enzymology, 1985, vol. 115, pp. 55-77.
Li, C. et al., "Olefination of Ketenes for the Enantioselective Synthesis of Allenes via an Ylide Route," Tetrahedron, 2007, vol. 63, pp. 8046-8053.
Lieberman H. et al., Editors, "Pharmaceutical Dosage Forms," vol. 1, Marcel Dekker, Inc., 1980, Table of Contents (5 pages).
Llinas-Brunet M. et al., "Peptide-Based Inhibitors of the Hepatitis C Virus Serine Protease," Bioorganic & Medicinal Chemistry Letters, 1998, vol. 8 (13), pp. 1713-1718.
Louie J. et al., "Palladium-Catalyzed Amination of Aryl Triflates and Importance of Triflate Addition Rate," Journal of Organic Chemistry, 1997, vol. 62 (5), pp. 1268-1273.
Lu, L. et al., "Mutations Conferring Resistance to a Potent Hepatitis C Virus Serine Protease Inhibitor in Vitro," Antimicrobial Agents and Chemotherapy, 2004, vol. 48 (6), pp. 2260-2266.
Lucas S. et al.,"In Vivo Active Aldosterone Synthase Inhibitors with Improved Aelectivity: Lead Optimization Providing a Series of Pyridine Substituted 3,4-Dihydro-1 HQuinolin-2-one Derivatives," Journal of Medicinal Chemistry, 2008, vol. 51 (24), pp. 8077-8087.
Marti-Renom M.A. et al., "Comparative Protein Structure Modeling of Genes and Genomes," Annual Review of Biophysics and Biomolecular Structure, 2000, vol. 29, pp. 291-325.
Maschke A. "Excipients & Activities for Pharma", ExAct, No. 20, May 2008, Publisher BASF SE, 16 pages.
Masui M. et al., "A Practical Method for Asymmetric Borane Reduction of Prochiral Ketones Using Chiral Amino Alcohols and Trimethyl Borate," Synlett, 1997, vol. 1997 (3), pp. 273-274.

(56) References Cited

OTHER PUBLICATIONS

Matzeit A. et al., "Radical Tandem Cyclizations by Anodic Decarboxylation of Carboxylic Acids," Synthesis, 1995, vol. 1995 (11), pp. 1432-1444.
Mercer D.F. et al., "Hepatitis C Virus Replication in Mice with Chimeric Human Livers," Nature Medicine, 2001, vol. 7 (8), pp. 927-933.
Miranker A. et al., "Functionality Maps of Binding Sites: A Multiple Copy Simultaneous Search Method," Proteins: Structure, Function, and Genetics, 1991, vol. 11 (1), pp. 29-34.
Misra M. et al., "Organocatalyzed Highly Atom Economic One Pot Synthesis of Tetrahydropyridines as Antimalarials," Bioorganic & Medicinal Chemistry, 2009, vol. 17, pp. 625-633.
Moinet C. et al., "Novel Non-Peptide Ligands for the Somatostatin sst3 Receptor," Bioorganic & Medicinal Chemistry Letters, 2001, vol. 11 (8), pp. 991-995.
Muci A.R. et al., "Practical Palladium Catalysts for C-N and C-0 Bond Formation," Topics in Current Chemistry, 2002, vol. 219, pp. 131-209.
Muller C.E. "Prodrug Approaches for Enhancing the Bioavailability of Drugs with Low Solubility," Chemistry & Biodiversity, 2009, vol. 6 (11), pp. 2071-2083.
Muri E.M.F. et al., "Pseudo-Peptides Derived From Isomannide as Potential Inhibitors of Serine Proteases," Amino Acids, 2005, vol. 28 (4), pp. 413-419.
Navaza J. "AMoRe: An Automated Package for Molecular Replacement," Acta Crystallographica, 1994, vol. A50 (2), pp. 157-163.
Naylor E.M. et al., "3-Pyridylethanolamines: Potent and Selective Human β3 Adrenergic Receptor Agonists," Bioorganic & Medicinal Chemistry Letters, 1998, vol. 8 (21), pp. 3087-3092.
Nevar N.M. et al., "One Step Preparation of 1,4-Diketones from Methyl Ketones and a-Bromomethyl Ketones in the Presence of ZnC12•t-BuOH•Et2NR as a Condensation Agent," Synthesis, 2000, vol. 9, pp. 1259-1262.
Nishibata Y. et al., "Confirmation of Usefulness of a Structure Construction Program Based on Three-Dimensional Receptor Structure for Rational Lead Generation," Journal of Medicinal Chemistry, 1993, vol. 36 (20), pp. 2921-2928.
Pak V.D. et al., "Catalytic Condensation of Schiff's Base with P-Methoxybenzal Acetone," Catalytic Synthesis of Organic Nitrate Compounds, 1970, vol. 68 (Part 4), pp. 66-71.
Peng T. et al., "Construction of a Library of Rhodol Fluorophores for Developing New Fluorescent Probes," Organic Letters, 2010, vol. 12 (3), pp. 496-499.
Penning T.D. et al, "Discovery and SAR of 2-(1-Propylpiperidin-4-yl)-1 H-Benzimidazole-4-Carboxamide: A Potent Inhibitor of Poly(ADP-ribose) Polymerase (PARP) for the Treatment of Cancer," Bioorganic & Medicinal Chemistry, 2008, vol. 16(14), pp. 6965-6975.
Rancourt J. et al., "Peptide-Based Inhibitors of the Hepatitis C Virus NS3 Protease: Structure-Activity Relationship at the C-Terminal Position," Journal of Medicinal Chemistry, 2004, vol. 47 (10), pp. 2511-2522.
Rao S.N. et al., "Validation Studies of the Site-Directed Docking Program LibDock," Journal of Chemical Information and Modeling, 2007, vol. 47 (6), pp. 2159-2171.
Rarey M. et al., "A Fast Flexible Docking Method using an Incremental Construction Algorithm," Journal of Molecular Biology, 1996, vol. 261 (3), pp. 470-489.
Reintjes T. Editor "Solubility Enhancement with BASF Pharma Polymers: Solubilizer Compendium," BASF SE, Pharma Ingredients & Services, Lampertheim, Germany, Oct. 2011 (130 pages). Submitted in two parts due to size.
Ronn R. et al., "Exploration of Acyl Sulfonamides as Carboxylic Acid Replacements in Protease Inhibitors of the Hepatitis C Virus Full-length N53," Bioorganic & Medicinal Chemistry Letters, 2006, vol. 14 (2), pp. 544-559.
Rosen M.H. et al., "Contraceptive Agents from Cycloaddition Reactions of Diarylcyclopropenones and Diarylthiirene 1,1-Dioxides," Journal of Medicinal Chemistry, 1976, vol. 19 (3), pp. 414-419.
Rossmann M.G., "The Molecular Replacement Method: A Collection of Papers on the Use of Non-Crystallographic Symmetry" Gordon and Breach Science Publishers, 1972, Table of Contents, 6 pages.
Sali A. et al., "Comparative Protein Modelling by Satisfaction of Spatial Restraints," Journal of Molecular Biology, 1993, vol. 234 (3), pp. 779-815.
Sato H. et al., "Prediction of Multiple Binding Modes of the CDK2 Inhibitors, Anilinopyrazoles, Using the Automated Docking Programs GOLD, FlexX, and LigandFit: An Evaluation of Performance," Journal of Chemical Information and Modeling, 2006, vol. 46 (6), pp. 2552-2562.
Sato M. et al., "Efficient Preparation of Optically Pure C2-Symmetrical Cyclic Amines for Chiral Auxiliary," Synthesis, 2004, vol. 9, pp. 1434-1438.
Sawyer J.S. et al., "Synthetic and Structure/Activity Studies on Acid-Substituted 2-Arylphenols:Discovery of 2-[2-Propyl-3-[3-[2-ethyl-4-(4-fluorophenyl)-5-hydroxyphenoxy]-propoxy]phenoxy]benzoic Acid, a High-Affinity Leukotriene B4 Receptor Antagonist," Journal of Medicinal Chemistry, 1995, vol. 38 (22), pp. 4411-4432.
Serajuddin A.T.M., "Solid Dispersion of Poorly Water-Soluble Drugs: Early Promises, Subsequent Problems, and Recent Breakthroughs," Journal of Pharmaceutical Sciences, 1999, vol. 88 (10), pp. 1058-1066.
Singh Y. et al., "Recent Trends in Targeted Anticancer Prodrug and Conjugate Design," Current Medical Chemistry, 2008, vol. 15 (18), pp. 1802-1826.
Smith A.B. et al., "Indole Diterpene Synthetic Studies: Development of a Second-Generation Synthetic Strategy for (+)-Nodulisporic Acids A and B," Journal of Organic Chemistry, 2007, vol. 72 (13), pp. 4611-4620.
Smith D.C. et al., "Reissert Compound Chemistry. XXVI. The Syntheses of Bis-Benzvlisoquinolines," Journal of Heterocyclic Chemistry, 1976, vol. 13, pp. 573-576.
SOLUPLUS®, Technical Information, BASF Chemical Company, Pharma Ingredients & Services, Jul. 2010 Issue (8 pages).
Sousa S.F. et al., "Protein-Ligand Docking: Current Status and Future Challenges," Proteins: Structure, Function, and Bioinformatics, 2006, vol. 65 (1), pp. 15-26.
Sperling L. H. Editor, "Introduction to Physical Polymer Science," 2nd Edition, John Wiley & Sons, Inc., 1992, Table of Contents.
Sree Giri Prasad.B. et al., "Formulation and Evaluation of Oro Dispersible Tablets of Stavudine by Direct Compression Technique", Der Pharmacia Lettre, 2012, vol. 4 (5), pp. 1505-1514.
Sugawara M. et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119 (49), pp. 11986-11987.
Takagi S. et al., "Antimicrobial Agents From Bletilla Striata," Phytochemistry, 1983, vol. 22 (4), pp. 1011-1015.
Tatsumi K. et al., "Enzyme-Mediated Coupling of 3,4-Dichloroaniline and Ferulic Acid: A Model for Pollutant Binding to Humic Materials," Environmental Science & Technology, 1994, vol. 28, pp. 210-215.
Tellinghuisen T.L. et al., "Structure of the Zinc-Binding Domain of an Essential Component of the Hepatitis C Virus Replicase," Nature, 2005, vol. 435 (7040), pp. 374-379.
Testa B. et al., "Prodrug Research: Futile or Fertile?," Biochemical Pharmacology, 2004, vol. 68, pp. 2097-2106.
Thayer A. M., "Finding Solutions, Custom manufacturers take on drug solubility issues to help pharmaceutical firms move products through development," Chemical & Engineering News, 2010, vol. 88 (22), pp. 13-18.
Tsantrizos Y.S. et al., "Macrocyclic Inhibitors of the NS3 Protease as Potential Therapeutic Agents of Hepatitis C Virus Infection," Angewandte Chemie International Edition, 2003, vol. 42 (12), pp. 1355-1360.

(56) References Cited

OTHER PUBLICATIONS

Vagin A. et al., "MOLREP: An Automated Program for Molecular Replacement," Journal of Applied Crystallography, 1997, vol. 30, pp. 1022-1025.
Vallee M.R.J. et al., "Photoannelation Reactions of 3-(Alk-1-ynyl)cyclohept-2-en-1-ones," Helvetica Chimica Acta, 2010, vol. 93 (1), pp. 17-24.
Verboom W. et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49 (2), pp. 269-276.
Warren G.L. et al., "A Critical Assessment of Docking Programs and Scoring Functions," Journal of Medicinal Chemistry, 2006, vol. 49 (20), pp. 5912-5931.
Willis M.C. et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.
Wolfe J.P. et al., "Palladium-Catalyzed Amination of Aryl Triflates," Journal of Organic Chemistry, 1997, vol. 62 (5), pp. 1264-1267.
Written Opinion for Application No. PCT/US2011/027511, dated Nov. 10, 2011, 6 pages.
Wu G.Y. et al., "A Novel Immunocompetent Rat Model of HCV Infection and Hepatitis," Gastroenterology, 2005, vol. 128 (5), pp. 1416-1423.
Xiao D. et al., "A Practical Synthetic Pathway to Polysubstituted Tetrahydropyridines via Multicomponent Reactions Catalyzed by BF3•0Et2," Synlett, 2005, vol. 10, pp. 1531-1534.
Xie Z.C. et al., "Transmission of Hepatitis C Virus Infection to Tree Shrews," Virology, 1998, vol. 244 (2), pp. 513-520.
Yanagi M. et al., "Transcripts from a Single Full-Length cDNA Clone of Hepatitis C Virus are Infectious when Directly Transfected into the Liver of a Chimpanzee," Proceedings of the National Academy of Sciences, 1997, vol. 94 (16), pp. 8738-8743.
Yu H. et al., "The Discovery of Novel Vascular Endothelial Growth Factor Receptor Tyrosine Kinases Inhibitors: Pharmacophore Modeling, Virtual Screening and Docking Studies," Chemical Biology and Drug Design, 2007, vol. 69 (3), pp. 204-211.
Zhang J. et al., "Stereoselective Bromination-Suzuki Cross-Coupling of Dehydroamino Acids to Form Novel Reverse-Turn Peptidomimetics: Substituted Unsaturated and Saturated Indolizidinone Amino Acids," Organic Letters, 2002, vol. 4(23), pp. 4029-4032.
Zhu Q. et al., "Novel Robust Hepatitis C Virus Mouse Efficacy Model," Antimicrobial Agents and Chemotherapy, 2006, vol. 50 (10), pp. 3260-3268.
Chiou et al., "Pharmaceutical applications of solid dispersion systems," J. Pharm. Sci., 60(9): 1281-1302 (1971).
Food and Drug Administration Guidance for Industry, SUPAC-IR/MR: Immediate Release and Modified Release Solid Oral Dosage Forms, Manufacturing Equipment Addendum, Jan. 1999, CMC 9, Revision 1, (44 pages).
Masters, K., Spray Drying Handbook, Halstead Press, New York, 4th ed., 1985 (Table of Contents only, 7 pages).
Written Opinion from PCT/US2015/010060, dated Mar. 27, 2015 (6 pages).
International Search Report from PCT/US2015/010060, dated Mar. 27, 2015 (6 pages).
Co-pending U.S. Appl. No. 12/858,221, filed Aug. 17, 2010.
Co-pending U.S. Appl. No. 12/008,668, filed Oct. 19, 2012.
Co-pending U.S. Appl. No. 12/941,299, filed Nov. 8, 2010.
Co-pending U.S. Appl. No. 13/045,136, filed Mar. 10, 2011.
Co-pending U.S. Appl. No. 13/045,263, filed Mar. 10, 2011.
Co-pending U.S. Appl. No. 13/072,538, filed Mar. 25, 2011.
Co-pending U.S. Appl. No. 13/072,550, filed Mar. 25, 2011.
Co-pending U.S. Appl. No. 13/113,601, filed May 23, 2011.
Co-pending U.S. Appl. No. 13/115,565, filed May 25, 2011.
Co-pending U.S. Appl. No. 13/544,576, filed Jul. 9, 2012.
Co-pending U.S. Appl. No. 13/544,634, filed Jul. 9, 2012.
Co-pending U.S. Appl. No. 13/603,006, filed Sep. 4, 2012.
Co-pending U.S. Appl. No. 13/603,022, filed Sep. 4, 2012.
Co-pending U.S. Appl. No. 13/656,012, filed Oct. 19, 2012.
Co-pending U.S. Appl. No. 13/656,024, filed Oct. 19, 2012.
Wyles, D.L., et al, "Synergy of small molecular inhibitors of hepatitis C virus replication directed at multiple viral targets,"J Virol. Mar. 2007;81 (6):3005-8. Epub Dec. 20, 2006.
Einav S., et al, "The hepatitis C virus (HCV) NS4B RNA binding inhibitor clemizole is highly synergistic with HCV protease inhibitors,"J Infect Dis. Jul. 1, 2010; 202 (1):65-74.
Grunberger, et al, "3-Drug Synergistic Interaction of Small Molecular Inhibitors of Hepatitis C Virus Replication," Journal of Infectious Diseases 2008;197:42-45.
Koev, et al, "Antiviral interactions of an HCV polymerase inhibitor with an HCV protease inhibitor or interferon in vitro," Antiviral Res. Jan. 2007; 73(1):78-83. Epub Aug. 17, 2006.

\* cited by examiner

COMPOSITIONS AND METHODS FOR TREATING HCV

CROSS-REFERENCE TO RELATED PATENT APPLICATION

This patent application is a continuation of U.S. patent application Ser. No. 13/474,411 filed May 17, 2012, which claims priority to U.S. Provisional Patent Application No. 61/486,842, filed May 17, 2011. The entire text of these applications is incorporated by reference into this patent application.

TECHNICAL FIELD

This disclosure is directed to: (a) pharmaceutical compositions that comprise two or more therapeutic agents that, inter alia, are useful for inhibiting hepatitis C virus (HCV); (b) methods for preparing such compositions; and (c) methods of use of such compositions; as well as (d) methods for inhibiting HCV by co-administering two or more anti-HCV therapeutic agents.

BACKGROUND

Hepatitis C is a blood-borne, infectious, viral disease that is caused by an RNA virus belonging to the Hepacivirus genus in the Flaviviridae family called HCV. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer (hepatocellular carcinoma), and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear the virus without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed. Following treatment with a combination of pegylated interferon alpha and ribavirin, sustained cure rates (sustained viral response) of about 75% occur in people with HCV genotypes 2 and 3 in 24 weeks of treatment, about 50% in those with HCV genotype 1 with 48 weeks of treatment, and about 65% in those with HCV genotype 4 in 48 weeks of treatment.

Thus, there continues to be a need for new compositions and methods of treatment to prevent the progression of liver damage from hepatitis C. This disclosure provides compositions and methods of treatment that generally address such a need.

SUMMARY

This disclosure is directed, in part, to the co-administration of an amount of therapeutic agent A with an amount of therapeutic agent B. Therapeutic agent A is compound A or a salt thereof:

compound A

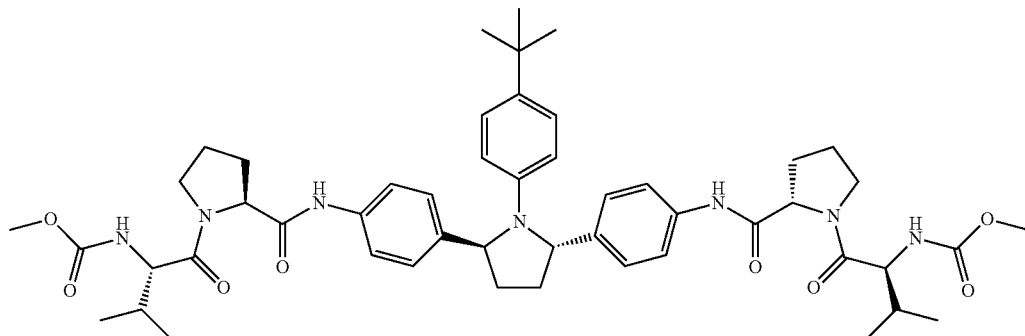

Therapeutic agent B is compound B or a salt thereof:

compound B

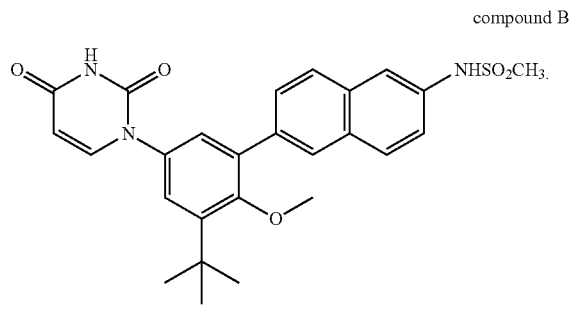

This disclosure is also directed, in part, to combinations or pharmaceutical compositions comprising therapeutic agent A and therapeutic agent B. The combinations or compositions may comprise one or more additional therapeutic agents.

This disclosure is also directed, in part, to methods for treating hepatitis C in a subject in need of such treatment. The methods comprise administering to the subject an amount of therapeutic agent A and an amount of therapeutic agent B. The methods may optionally comprise administering to the subject an amount of one or more additional therapeutic agents.

This disclosure is also directed, in part, to the use of therapeutic agent A and therapeutic agent B, to prepare a medicament. In embodiments, the medicament is useful for treating hepatitis C.

This disclosure is also directed, in part, to methods of using therapeutic agent A and therapeutic agent B, for example, to inhibit replication of a ribonucleic acid (RNA) virus (including HCV) or to treat a disease treatable by inhibiting HCV RNA polymerase and/or the NS5A protein of HCV.

Further benefits of the disclosed embodiments will be apparent to one skilled in the art from reading this disclosure.

BRIEF DESCRIPTION OF THE DRAWINGS

FIG. 1 details the mean differences between the observed anti-HCV effect and the calculated additivity of that effect in percent inhibition at various concentrations of compound A and compound B according to the Prichard and Shipman model. The concentrations for each of compound A and compound B are expressed in a $\log_2$ scale.

DETAILED DESCRIPTION

Figure 1:
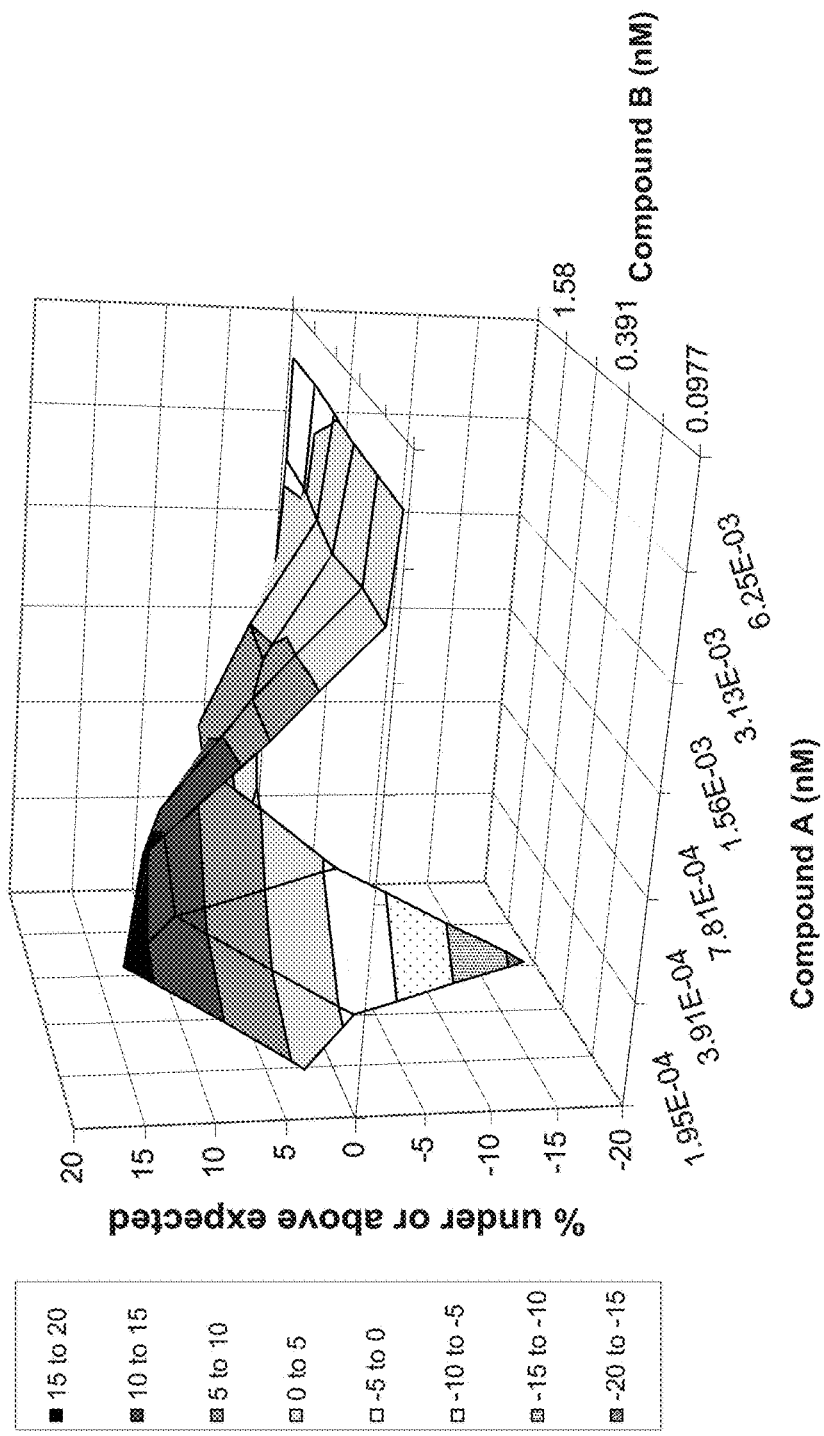
FIG. 1 is a three-dimensional surface plot illustrating the statistically significant anti-HCV effect for the combination of compound A and compound B in the HCV Genotype 1b (Con1) replicon.

This detailed description is intended only to acquaint others skilled in the art with the disclosed embodiments, their principles, and their practical applications so that others skilled in the art may adapt and apply the disclosed embodiments in their numerous forms, as they may be best suited to the requirements of a particular use. This description and its specific examples are intended for purposes of illustration only. This disclosure, therefore, is not limited to the embodiments described in this patent application, and may be variously modified.

The disclosure is directed, in part, to the co-administration of an amount of therapeutic agent A with an amount of therapeutic agent B. Therapeutic agent A is compound A or a salt thereof.

compound A

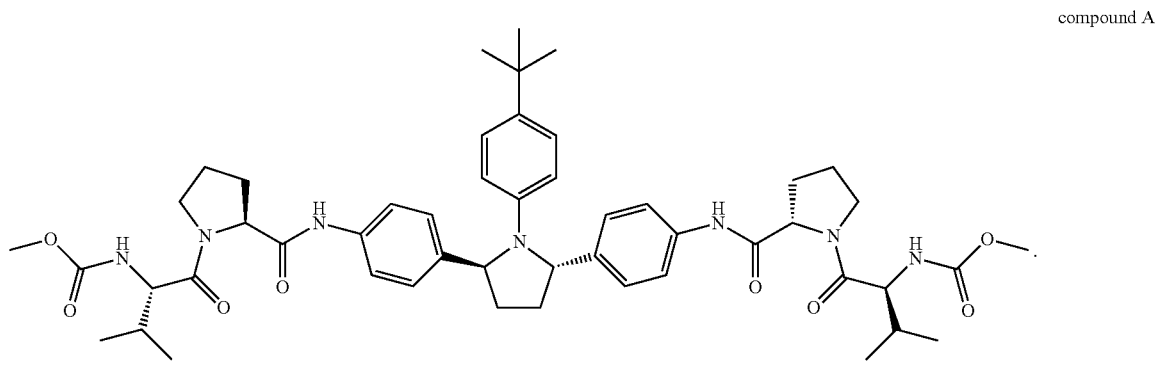

Compound A is also known as dimethyl (2S,2'S)-1,1'-((2S, 2'S)-2,2'-(4,4'-((2S,5S)-1-(4-tert-butylphenyl)pyrrolidine-2, 5-diyl)bis(4,1-phenylene))bis(azanediyl)bis(oxomethylene) bis(pyrrolidine-2,1-diyl))bis(3-methyl-1-oxobutane-2,1-diyl)dicarbamate. Compound A can be prepared as described in, for example, U.S. Publication No. 2010/0317568, which is incorporated herein by reference.

Therapeutic agent B is compound B or a salt thereof.

compound B

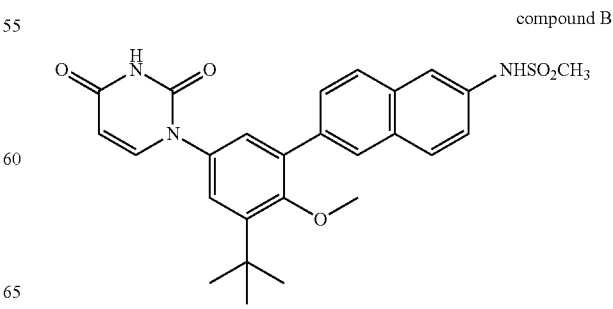

Compound B is also known as N-(6-(3-tert-butyl-5-(2,4-dioxo-3,4-dihydropyrimidin-1(2H)-yl)-2-methoxyphenyl) naphthalen-2-yl)methanesulfonamide. As described in, for example, International Publication No. WO2009/039127, therapeutic agent B includes various salts of compound B, such as sodium salts, potassium salts, and choline salts. Therapeutic agent B also includes crystalline forms of compound B and its salts such as solvate, hydrate, and solvent-free crystalline forms of compound B and its salts. Compositions comprising compound B can be prepared as described in, for example, International Publication No. WO2009/039127 which is incorporated herein by reference.

The total daily dose of the disclosed compounds or their salts (administered in single or divided doses) may typically be from about 0.001 mg/kg to about 200 mg/kg, or from about 0.001 mg/kg to about 30 mg/kg, or from about 0.01 mg/kg to about 10 mg/kg (i.e., mg of the compound or salt per kg body weight).

Therapeutic agent A may be administered, for example and without limitation, as a free acid or salt. Therapeutic agent A may be administered in any suitable amount such as, for example, in doses of from about 0.1 mg/kg to about 200 mg/kg body weight, or from about 0.25 mg/kg to about 100 mg/kg, or from about 0.3 mg/kg to about 3.0 mg/kg. As non-limiting examples, therapeutic agent A may be administered in a total daily dose amount of from about 5 mg to about 300 mg, or from about 25 mg to about 200 mg, or from about 25 mg to about 50 mg. In embodiments, the total daily dosage amount for therapeutic agent A is about 25 mg. In embodiments, the total daily dosage amount for therapeutic agent A is about 50 mg.

Therapeutic agent B may be administered as a free acid, salt or particular crystalline form of compound B. In embodiments, therapeutic agent B is administered as a sodium salt of compound B. Therapeutic agent B may be administered in any suitable amount such as, for example, in doses of from about 5 mg/kg to about 30 mg/kg. As non-limiting examples, therapeutic agent B may be administered in a total daily dose amount of from about 300 mg to about 1800 mg, or from about 400 mg to about 1600 mg, or from about 600 mg to about 1800 mg, or from about 800 mg to about 1600 mg. In embodiments, the total daily dosage amount for therapeutic agent B is about 300 mg. In embodiments, the total daily dosage amount for therapeutic agent B is about 400 mg. In embodiments, the total daily dosage amount for therapeutic agent B is about 600 mg. In embodiments, the total daily dosage amount for therapeutic agent B is about 800 mg. In embodiments, the total daily dosage amount for therapeutic agent B is about 1200 mg. In embodiments, the total daily dosage amount for therapeutic agent B is about 1600 mg.

Therapeutic agent A and therapeutic agent B may also be co-administered with interferon. Interferon may include any suitable form of interferon such as interferon alpha, interferon alpha 2a, interferon alpha 2b such as LOCTERON®, interferon omega, interferon lambda, and albinterferon, such as ZALBIN® and JOULFERON® or albinterferon as disclosed in International Publication No. WO2007/021494A2. In embodiments, the interferon is pegylated. Pegylated interferon may include pegylated interferon alpha 2a, such as PEGASYS®, or pegylated interferon alpha 2b, such as PEGINTRON®; pegylated interferon omega, such as Biomed-510, or pegylated interferon omega as disclosed in U.S. Publication No. 2006/263433; and pegylated interferon lambda, such as PEG-rIL-29, or pegylated interferon lambda as disclosed in International Publication No. WO2007/041713A1.

Interferon may be administered in accordance with interferon administration well known in the art. For example, interferon may be administered in a total weekly dose amount of from about 0.1 mcg/kg to about 2.5 mcg/kg. In embodiments, alpha-2b pegylated interferon is administered in a total weekly dose of about 0.5 mcg/kg to about 1.5 mcg/kg. Interferon may be administered in a total weekly dose amount of 50 mcg to about 250 mcg. In embodiments, alpha-2a pegylated interferon is administered in a total weekly dose of from about 90 mcg to about 180 mcg.

LOCTERON® is an example of an interferon that can be co-administered with the disclosed compositions, compounds and their salts. LOCTERON® is a controlled-release formulation of interferon alpha-2b interferon that allows the interferon to be administered every two weeks rather than every week. LOCTERON® may be administered in accordance with LOCTERON® administration well known in the art. For example, the interferon may be administered at least once every one to two weeks at a dose of from about 250 mcg to about 750 mcg or from about 320 mcg to about 640 mcg as a single or as multiple subcutaneous injections at the same or different doses in each injection. In embodiments, the peginterferon is administered subcutaneously at a dose of 480 mcg every two weeks.

ZALBIN® and JOULFERON® (formerly known as Albuferon® and ABF-656) are other examples of an interferon that can be co-administered with the disclosed compositions, compounds and their salts. ZALBIN® and JOULFERON® are an albumin interferon alpha-2b which is a recombinant fusion protein composed of recombinant human albumin genetically fused at its C-terminus to the N-terminus of recombinant human interferon alfa-2b. ZALBIN® and JOULFERON® may be administered in accordance with ZALBIN® and JOULFERON® administration well known in the art. For example, the albinterferon may be administered at least once every one to two weeks at a dose of from about 1 to about 2000 mcg as a single or as multiple subcutaneous injections at the same or different doses in each injection. In embodiments, the albinterferon is administered subcutaneously at a dose of from about 7 to about 900 mcg as single or double (14 days apart) injections.

PEGASYS® is a further example of an interferon that can be co-administered with the disclosed compositions, compounds and their salts. PEGASYS® is a pegylated interferon alpha-2a which is a covalent conjugate of recombinant alfa-2a interferon with a single branched bis-monomethoxy polyethylene glycol (PEG) chain. PEGASYS® may be administered in accordance with PEGASYS® administration well known in the art. For example, the peginterferon may be administered at least once every one to two weeks at a dose of from about 100 mcg to about 400 mcg as a single or as multiple subcutaneous injections at the same or different doses in each injection. In embodiments, the peginterferon is administered subcutaneously at a dose of about 180 mcg as a single weekly injection.

PEGINTRON® is an additional example of an interferon that can be co-administered with the disclosed compositions, compounds and their salts. PEGINTRON® is a pegylated interferon alpha-2b which is a covalent conjugate of recombinant alpha-2b interferon with monomethoxy polyethylene glycol (PEG). PEGINTRON® may be administered in accordance with PEGINTRON® administration well known in the art. For example, the peginterferon may be administered at least once every one to two weeks at a dose of from about 1 mcg/kg to about 3 mcg/kg or from about 40 mcg/m$^2$ to about 80 mcg/m$^2$. The peginterferon may be administered at least once every one to two weeks at a dose of from about 25 mcg to about 200 mcg or from about 50 mcg to about 150 mcg as a single or as multiple subcutaneous injections at the same or different doses in each injection. In embodiments, the peginterferon is administered subcutaneously at a dose of about 1.5 mcg/kg as single weekly injection. In embodiments, the peginterferon is administered subcutaneously at a dose of about 60 mcg/m$^2$ as single weekly injection.

Therapeutic agent A and therapeutic agent B may also be co-administered with ribavirin, or a pro-drug thereof, in the same or separate pharmaceutical compositions. Ribavirin may include any suitable form or formulation of ribavirin. Exemplary formulations of ribavirin include COPEGUS®, REBETOL® and RIBASPHERE®. An exemplary pro-drug of ribavirin is taribavirin having the chemical name of 1-β-D-ribofuranosyl-1,2,4-triazole-3-carboxamidine.

Ribavirin and taribavirin may be administered in accordance with ribavirin and taribavirin administration well known in the art. For example, ribavirin or taribavirin may be administered in a total daily dose of from about 5 mg to about 1500 mg. In embodiments, COPEGUS® or REBETOL® is administered in a daily dosage amount of from about 500 mg to about 1500 mg in one dose or in divided doses. In embodiments, COPEGUS® or REBETOL® is administered in a daily dosage amount of about 800 mg. In embodiments, REBETOL® is administered in a daily dosage amount of about 1000 mg. In embodiments, COPEGUS® or REBETOL® is administered in a daily dosage amount of about 1200 mg. In embodiments, REBETOL® is administered in a daily dosage amount of about 1400 mg.

Ribavirin may be co-administered with the interferon, together with therapeutic agent A and therapeutic agent B. In embodiments, ribavirin is administered with pegylated interferon alpha 2a, such as PEGASYS®, together with therapeutic agent A and therapeutic agent B. For example, in embodiments, a daily dose of COPEGUS® of 800 mg to 1200 mg is administered in combination with a weekly dose of PEGASYS® of 180 mcg, together with daily administration of therapeutic agent A and therapeutic agent B. In embodiments, ribavirin is administered with pegylated interferon alpha 2b, such as PEGINTRON®, together with therapeutic agent A and therapeutic agent B. For example, in embodiments, a daily dose of REBETOL® of 800 mg to 1400 mg is administered in combination with a weekly dose of PEGINTRON® of 1.5 mcg/kg, together with daily administration of therapeutic agent A and therapeutic agent B.

Therapeutic agent A and therapeutic agent B may be co-administered with interferon and ribavirin or a pro-drug thereof.

Therapeutic agent A and therapeutic agent B may be co-administered with an HIV inhibitor including an HIV protease inhibitor, with or without a cytochrome P-450 inhibitor (e.g., ritonavir), in the same or separate pharmaceutical compositions.

The cytochrome P-450 inhibitor may be administered in any suitable amount such as, for example, in doses of from about 0.3 mg/kg to about 2 mg/kg or from about 0.6 mg/kg to about 1.5 mg/kg. As non-limiting examples, the cytochrome P-450 inhibitor may be administered in a total daily dose amount of from about 25 mg to about 300 mg, or from about 50 mg to about 250 mg, or from about 100 mg to about 200 mg. In embodiments, the cytochrome P-450 inhibitor is administered in a total daily dose amount of about 25 mg. In embodiments, the cytochrome P-450 inhibitor is administered in a total daily dose amount of about 50 mg. In embodiments, the cytochrome P-450 inhibitor is administered in a total daily dose amount of about 75 mg. In embodiments, the cytochrome P-450 inhibitor is administered in a total daily dose amount of about 100 mg. In embodiments, the cytochrome P-450 inhibitor is administered in a total daily dose amount of about 125 mg.

Therapeutic agent A and therapeutic agent B may be co-administered with an HCV protease inhibitor in the same or separate pharmaceutical compositions. HCV protease inhibitors may include, for example, ACH-1625 (Achillion), ACH-2684 (Achillion), AVL-181 (Avila Therapeutics), AVL-192 (Avila Therapeutics), BI 201335 (Boehringer Ingelheim), BMS-791325 (Bristol-Myers Squibb), GS 9256 (Gilead), IDX320 (Idenix), danoprevir or ITMN-191 or R7227 (RO5190591) (Intermune/Roche), TMC435 (Medivir/Tibotec/JnJ), Boceprevir or SCH503034 (Merck), Vaniprevir or MK-7009 (Merck), PHX1766 (Phenomix), Telaprevir or VX-950 (Vertex), VX-985 (Vertex) and VX-500 (Vertex).

In embodiments, therapeutic agent A and therapeutic agent B are co-administered with interferon and an HCV protease inhibitor. In embodiments, therapeutic agent A and therapeutic agent B are co-administered with ribavirin and an HCV protease inhibitor. In embodiments, therapeutic agent A and therapeutic agent B are co-administered with interferon, ribavirin and an HCV protease inhibitor. In embodiments, therapeutic agent A and therapeutic agent B are co-administered with an HCV protease inhibitor (with or without a cytochrome P-450 inhibitor such as ritonavir). In embodiments, therapeutic agent A and therapeutic agent B are co-administered with ribavirin and an HCV protease inhibitor (with or without a cytochrome P-450 inhibitor such as ritonavir). In embodiments, therapeutic agent A and therapeutic agent B are co-administered with interferon, ribavirin, and an HCV protease inhibitor (with or without a cytochrome P-450 inhibitor such as ritonavir).

Factors affecting the dosage regimen include the route of administration; the type, age, weight, sex, diet, and condition of the patient; the severity of the pathological condition; pharmacological considerations, such as the activity, efficacy, pharmacokinetic, and toxicology profiles of the particular compound or salt used; whether a drug delivery system is utilized; and the specific drug combination. Thus, the dosage regimen actually employed can vary widely and, therefore, can deviate from the disclosed dosage regimen set forth above.

In embodiments, the combination or pharmaceutical composition comprises an amount of therapeutic agent A and an amount of therapeutic agent B. The amount of therapeutic agent A and therapeutic agent B may be any suitable amount that provides the desired total periodic dosing amount such as the total daily dosing amount. For example, the amount of therapeutic agent A in the combination or pharmaceutical composition may be any suitable amount such as from about 5 mg to about 200 mg or from about 10 to about 100 mg or from about 25 mg to about 50 mg. In embodiments, the total daily dosage amount for therapeutic agent A is about 25 mg. In embodiments, the total daily dosage amount for therapeutic agent A is about 50 mg.

The amount of therapeutic agent B in the combination or pharmaceutical composition may be from about 100 mg to about 1800 mg or from about 300 to about 1600 mg or from about 400 mg to about 1200 mg. In embodiments, the amount of therapeutic agent B in a combination or pharmaceutical composition is about 100 mg. In embodiments, the amount of therapeutic agent B in a combination or pharmaceutical composition is about 200 mg. In embodiments, the amount of therapeutic agent B in a combination or pharmaceutical composition is about 300 mg. In embodiments, the amount of therapeutic agent B in a combination or pharmaceutical composition is about 400 mg. In embodiments, the amount of therapeutic agent B in a combination or pharmaceutical composition is about 600 mg. In embodiments, the amount of therapeutic agent B in a combination or pharmaceutical composition is about 800 mg. In embodiments, the amount of therapeutic agent B in a combination or pharmaceutical composition is about 1000 mg. In embodiments, the amount of therapeutic agent B in a combination or pharmaceutical composition is about 1200 mg. In embodiments, the amount of therapeutic agent B in a combination or pharmaceutical composition is about 1600 mg.

The combinations or pharmaceutical compositions may also comprise other therapeutic agents and combinations thereof, used to treat hepatitis C, such as any suitable amount of ribavirin and pro-drugs thereof, HCV inhibitors such as, for example, HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors; and HIV inhibitors.

In embodiments, the combination or pharmaceutical composition comprises an amount of therapeutic agent A and an amount of therapeutic agent B. In embodiments, the combination or pharmaceutical composition comprises an amount of therapeutic agent A, an amount of therapeutic agent B and an amount of HCV protease inhibitor. In embodiments, the combination or pharmaceutical composition comprises an amount of therapeutic agent A, an amount of therapeutic agent B and ribavirin. In embodiments, the combination or pharmaceutical composition comprises an amount of therapeutic agent A, an amount of therapeutic agent B, and an amount of HCV protease inhibitor (with or without a cytochrome P-450 inhibitor such as ritonavir). In embodiments, the combination or pharmaceutical composition comprises an amount of therapeutic agent A, an amount of therapeutic agent B, an amount of HCV protease inhibitor (with or without a cytochrome P-450 inhibitor such as ritonavir), and ribavirin. In embodiments, interferon is co-administered with the above-mentioned combination or pharmaceutical composition.

Dosage unit compositions may contain such amounts or submultiples thereof to make up the total daily dose. The administration of the therapeutic agent may be repeated a plurality of times. Multiple doses per day may be used to achieve the total daily dose, if desired. For example, a combination or pharmaceutical composition comprising a dose of about 25 mg or 50 mg of therapeutic agent A may be administered at least twice per day to achieve a total daily dosage amount of about 50 mg or 100 mg of therapeutic agent A, respectively. A dose of about 400 mg or 800 mg of therapeutic agent B may be administered at least twice per day to achieve a total daily dosage amount of about 800 mg or 1600 mg of therapeutic agent B, respectively.

The disclosed compositions may comprise one or more conventional pharmaceutically acceptable carriers, adjuvants, and/or vehicles (together referred to as "excipients"). The disclosed compositions may be prepared in a form for oral administration such as in a solid dosage form. Such solid dosage forms include, for example, capsules, tablets, pills, powders, and granules. In such solid dosage forms, the compounds or salts may be combined with one or more excipients. If administered per os, the compounds or salts may be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation, as may be provided in, for example, a dispersion of the compound or its salt in hydroxypropylmethyl cellulose. In the case of capsules, tablets, and pills, the dosage forms also may comprise buffering agents, such as sodium citrate, or magnesium or calcium carbonate or bicarbonate. In addition, tablets and pills may be prepared with enteric coatings or other sustained/delayed/controlled release excipients known in the art. In embodiments, therapeutic agent A may be formulated as described in U.S. Provisional Application No. 61/353,553, filed Jun. 10, 2010, which is incorporated herein by reference.

One or more of interferon, an HCV protease inhibitor (with or without a cytochrome P-450 inhibitor, such as ritonavir), and ribavirin may be co-administered with therapeutic agent A and therapeutic agent B.

The disclosed combination(s)/composition(s) may be administered at any suitable frequency such as at least three times daily (e.g., every 8 hours in a 24-hour period), at least two times daily (e.g., every 12 hours in a 24-hour period), at least once daily (e.g., once in a 24-hour period), or at least once weekly (e.g., once in a 7-day period).

This disclosure is also directed, in part, to methods of using the disclosed combination(s)/composition(s). The disclosed combination(s)/composition(s) may be used in a method for inhibiting replication of an RNA virus. In embodiments, the method comprises exposing the virus to a disclosed combination(s)/composition(s) and, optionally one or more additional therapeutic agents. The disclosed combination(s)/composition(s) may be administered with one or more of an HCV protease inhibitor (with or without a cytochrome P-450 inhibitor such as ritonavir), interferon and ribavirin in the same or separate pharmaceutical compositions to inhibit replication of an RNA virus. In embodiments, replication of the RNA virus is inhibited in vitro. In embodiments, replication of the RNA virus is inhibited in vivo. In embodiments, the RNA virus whose replication is being inhibited is a single-stranded, positive sense RNA virus. In embodiments, the RNA virus whose replication is being inhibited is a virus from the Flaviviridae family. In embodiments, the RNA virus whose replication is being inhibited is HCV.

The disclosed combination(s)/composition(s) may be used in a method for inhibiting HCV RNA polymerase. In embodiments, the method comprises exposing the polymerase to a disclosed combination(s)/composition(s) and, optionally one or more additional therapeutic agents. The disclosed combination(s)/composition(s) may be administered with one or more of an HCV protease inhibitor (with or without a cytochrome P-450 inhibitor such as ritonavir), interferon and ribavirin in the same or separate pharmaceutical compositions to inhibit HCV RNA polymerase. In embodiments, HCV RNA polymerase activity is inhibited in vitro. In embodiments, HCV RNA polymerase activity is inhibited in vivo.

The disclosed combination(s)/composition(s) may be used in a method for inhibiting the HCV non-structural protein 5A (NS5A protein). In embodiments, the method comprises exposing the polymerase to a disclosed combination(s)/composition(s) and, optionally one or more additional therapeutic agents. The disclosed combination(s)/composition(s) may be administered with one or more of an HCV protease inhibitor (with or without a cytochrome P-450 inhibitor such as ritonavir), interferon and ribavirin in the same or separate pharmaceutical compositions to inhibit the HCV NS5A protein. In embodiments, the HCV NS5A protein is inhibited in vitro. In embodiments, the HCV NS5A protein is inhibited in vivo.

The term "inhibiting" means reducing the level of RNA virus replication/HCV polymerase activity either in vitro or in vivo. For example, if a disclosed combination(s)/composition(s) reduces the level of RNA virus replication by at least about 10% compared to the level of RNA virus replication before the virus was exposed to the combination(s)/composition(s), then the combination(s)/composition(s) inhibits RNA virus replication. In some embodiments, the disclosed combination(s)/composition(s) can inhibit RNA virus replication by at least about 20%, at least about 30%, at least about 40%, at least about 50%, at least about 60%, at least about 70%, at least about 80%, at least about 90%, or at least about 95%.

The disclosed combination(s)/composition(s) may be used in a method for reducing HCV viral load. In embodiments, the method comprises exposing the polymerase to a disclosed combination(s)/composition(s) and, optionally one or more additional therapeutic agents. The disclosed combination(s)/composition(s) may be administered with one or more of an HCV protease inhibitor (with or without a cytochrome P-450 inhibitor such as ritonavir), interferon and ribavirin in the same or separate pharmaceutical compositions to reduce HCV viral load. In embodiments, HCV viral load is reduced in vitro. In embodiments, HCV viral load is reduced in vivo. For example, if a disclosed combination(s)/composition(s) reduces the HCV viral load by at least about 10% compared to the HCV viral load before the virus was exposed to the combination(s)/composition(s), then the combination(s)/composition(s) reduces the HCV viral load. In some embodiments, the disclosed combination(s)/composition(s) can reduce viral load by at least about 20%, at least about 30%, at least about 40%, at least about 50%, at least about 60%, at least about 70%, at least about 80%, at least about 90%, or at least about 95%.

The disclosed combination(s)/composition(s) may be used in a method for treating a disease that can be treated by inhibiting HCV RNA polymerase and/or the HCV NS5A protein. Thus, this disclosure is also directed, in part, to a method for treating hepatitis C in an animal in need of such treatment. These methods comprise administering to the animal a disclosed combination(s)/composition(s) and, optionally one or more additional therapeutic agents. The disclosed combination(s)/composition(s) may be administered with one or more of an HCV protease inhibitor (with or without a cytochrome P-450 inhibitor such as ritonavir), interferon and ribavirin in the same or separate pharmaceutical compositions to treat hepatitis C. In some embodiments, a therapeutically effective amount of the disclosed combination(s)/composition(s) is administered to the animal.

"Treating" means ameliorating, suppressing, eradicating, preventing, reducing the risk of, and/or delaying the onset of the disease being treated. The term "treating" encompasses administration of the disclosed combination(s)/composition(s) to an HCV-negative patient that is a candidate for an organ transplant.

The methods of treatment are particularly suitable for use with humans, but may be used with other animals, particularly mammals. A "therapeutically-effective amount" or "effective amount" is an amount that will achieve the goal of treating the targeted condition.

In embodiments, therapeutic agent A is administered in combination with therapeutic agent B to reduce side effects associated with the administration of an interferon and ribavirin, either alone or in combination.

This disclosure is also directed, in part, to use of the disclosed combination(s)/composition(s), and, optionally one or more additional therapeutic agents in preparation of a medicament for use in one or more of the disclosed methods. The disclosed combination(s)/composition(s) may be combined with one or more of an HCV protease inhibitor (with or without a cytochrome P-450 inhibitor such as ritonavir), interferon and ribavirin in the same or separate medicaments for use in one or more of the disclosed methods.

In embodiments, therapeutic agent A and therapeutic agent B are used in the preparation of a medicament. In embodiments, therapeutic agent A, therapeutic agent B and an HCV protease inhibitor (with or without a cytochrome P-450 inhibitor such as ritonavir) are used in the preparation of a medicament. In embodiments, therapeutic agent A, therapeutic agent B and ribavirin are used in the preparation of a medicament. In embodiments, therapeutic agent A, therapeutic agent B, an HCV protease inhibitor (with or without a cytochrome P-450 inhibitor such as ritonavir), and ribavirin are used in the preparation of a medicament.

In embodiments, the disclosed medicaments are for inhibiting replication of an RNA virus.

In embodiments, the disclosed medicaments are for inhibiting HCV RNA polymerase activity.

In embodiments, the disclosed medicaments are for inhibiting the HCV NS5A protein.

In embodiments, the disclosed medicaments are for decreasing HCV viral load in a subject.

In embodiments, the disclosed medicaments are for treating hepatitis C.

In embodiments, the disclosed medicaments are for reducing side effects associated with the administration of an interferon and ribavirin, either alone or in combination.

The disclosed medicaments may be for co-administration with one or more additional therapeutic agents. For example, the medicaments may be for co-administration with one or more of an HCV protease inhibitor (with or without a cytochrome P-450 inhibitor such as ritonavir), interferon and ribavirin.

In embodiments, the disclosed medicaments may be for co-administration with interferon. In embodiments, the disclosed medicaments are for co-administration with one or more of an HCV protease inhibitor (with or without a cytochrome P-450 inhibitor such as ritonavir), interferon and ribavirin for inhibiting replication of an RNA virus.

In embodiments, the disclosed medicaments are for co-administration with one or more of an HCV protease inhibitor (with or without a cytochrome P-450 inhibitor such as ritonavir), interferon and ribavirin for inhibiting HCV RNA polymerase activity.

In embodiments, the disclosed medicaments are for co-administration with one or more of an HCV protease inhibitor (with or without a cytochrome P-450 inhibitor such as ritonavir), interferon and ribavirin for inhibiting HCV NS5A protein.

In embodiments, the disclosed medicaments are for co-administration with one or more of an HCV protease inhibitor (with or without a cytochrome P-450 inhibitor such as ritonavir), interferon and ribavirin for decreasing HCV viral load in a subject.

In embodiments, the disclosed medicaments are for co-administration with one or more of an HCV protease inhibitor (with or without a cytochrome P-450 inhibitor such as ritonavir), interferon and ribavirin for treating hepatitis C.

EXAMPLES

The following examples are for illustration purposes and do not limit the scope of this disclosure in any way.

Materials.

The replicon cell line was derived from the human hepatoma cell line Huh7. It was derived from HCV genotype 1b (Con1), and is a bicistronic subgenomic replicon, essentially similar to those described in Science 285(5424):110-3 (1999). The first cistron of the construct contains a firefly luciferase reporter and a neomycin phosphotransferase selectable marker.

Replicon Cell Culture.

Replicon cells were seeded at a density of 5000 cells per well of a 96-well plate in 100 µl Dulbecco's Modified Eagle Media (DMEM) containing 5% FBS. Replicon cells were maintained in DMEM containing 100 IU/ml penicillin, 100 mg/ml streptomycin (Invitrogen), 200 mg/ml G418 (Invitrogen) and 10% fetal bovine serum (FBS) at 37° C. and 5% $CO_2$.

Combination Studies.

The replicon cell culture was used to determine the dose or concentration of therapeutic agent A that produces a synergistic, additive or antagonistic inhibitory effects on HCV replication when combined with therapeutic agent B.

The compounds were diluted in dimethyl sulfoxide (DMSO) to generate a 200× stock in a series of 6 two-fold dilutions. The dilution series was then further diluted 100-fold in the medium containing 5% FBS.

The dilutions of each compound were combined in a checkerboard fashion in the cell culture plates. Three experiments with three plates in each experiment were performed. In particular, six concentrations of compound A alone and six concentrations of the sodium salt of compound B alone were assayed in each plate. In addition, 36 combinations of various concentrations of the two compounds were assayed for each plate. The concentrations of compound A and compound B were chosen to ensure that the $EC_{50}$s of the compounds were substantially in the middle of the serial dilution range. For compound A, concentrations ranged from 0.0002 nM ($1.95 \times 10^{-4}$ nM) to 0.0063 nM ($6.25 \times 10^{-3}$ nM), and for compound B, concentrations ranged from 0.10 nM (0.0977 nM) to 3.13 nM. The cells were incubated in a tissue culture incubator at 37° C. and 5% $CO_2$ for three days.

The inhibitor effects of compounds on HCV replication were analyzed by determining the fraction of inhibition of the luciferase signal which was determined by measuring activity of a luciferase reporter gene using a Luciferase Assay System kit (Promega) according to the manufacturer's instructions. Passive Lysis buffer (30 µl, Promega) was added to each well, and the plates were incubated for 15 minutes with rocking to lyse the cells. Luciferin solution (100 µl, Promega) was added to each well and the luciferase activity was measured using a Victor II luminometer (Perkin-Elmer). To determine the $EC_{50}$, the luciferase inhibition data were analyzed using GraphPad Prism 4 software.

Combination Analysis.

Synergy or antagonism from combining therapeutic agent A with therapeutic agent B was quantified for direct comparison of inhibitor effects on HCV replication. The percent inhibition results were analyzed for synergy, additivity and antagonism according to the Bliss independence, Lowe additivity, and Pritchard-Direct models (Pharmacol. Rev. 47(2):331-85 (1995); Antiviral Research 14:181-206 (1990)).

An $E_{max}$ model in the following form is used to fit the data from each single drug for each plate in each experiment using the NLIN procedure of SAS (SAS 9.1, SAS Institute Inc. 2004), $$f_a = 1 - \frac{1}{\left(1 + \left(\frac{C}{I}\right)^h\right)^g},$$

where $f_a$ is the fraction of inhibition, C is the concentration, I is the location of the concentration-response curve's inflection point (point of greatest slope), g is the degree of asymmetry, and h is the shape parameter of the curve. Using the estimated g, I, and h for each single drug for each plate in an experiment, the fraction of inhibition for any concentration combination of the two drugs is predicted by one of two reference models: Loewe additivity and Bliss independence (Pharmacol. Rev. 47(2):331-85 (1995)). A difference between the actual observed fraction of inhibition and the predicted value is calculated for each concentration combination for each plate in each experiment to determine whether the observed combined effect is greater than that predicted by Loewe additivity or Bliss independence. For each concentration combination, the replicates (across all plates and experiments) were used to calculate a mean difference between observed and predicted fraction of inhibition, its standard error and its two-sided 95% confidence interval (CI).

The Prichard-Shipman method, similar to the $E_{max}$ methods, is used to calculate the difference between the actual observed fraction of inhibition and the predicted value for each concentration combination for each plate in each experiment to determine whether the observed combined effect is greater than the theoretical additive effect determined directly from the individual dose-response curves in the assays described above (Antiviral Research 14:181-206 (1990)). The calculated theoretical additivity is then compared to the experimental dose-response surface, and subsequently subtracted to reveal any areas of aberrant interaction. The following equation is used to calculate the theoretical additive effects:

$$Z = X + Y(1-X) = X + Y - XY,$$

where Z is the total inhibition produced by the combination of drugs X and Y, with X and Y representing the inhibition produced by drugs X and Y alone, respectively.

A difference between the actual observed fraction of inhibition and the predicted value is calculated for each concentration combination for each plate in each experiment to determine whether the observed combined effect is greater than the theoretical additive effect, Z, calculated from equation (1). The mean difference between the observed and predicted fraction of inhibition, its standard error and its two-sided 95% CI is then calculated for each concentration combination across all plates and experiments.

Synergy or antagonism for a concentration combination is determined by calculating at each concentration combination the 95% confidence interval (CI) of the mean difference between observed and predicted fraction of inhibition. If the lower bound of 95% CI is larger than zero, then the drug combination is considered to have a synergistic effect; if the upper bound of 95% CI is less than zero, then the drug combination is considered to have an antagonistic effect; otherwise, the effect of the combination is considered to be purely additive, and no significant antagonism or synergy exists at this concentration combination. Small differences of statistical significance caused by very small variance were excluded if the relative mean difference (i.e., the absolute mean difference divided by its corresponding observed mean inhibition) of the synergistic or antagonistic effect is less than about one percent.

Results.

Figure 2:
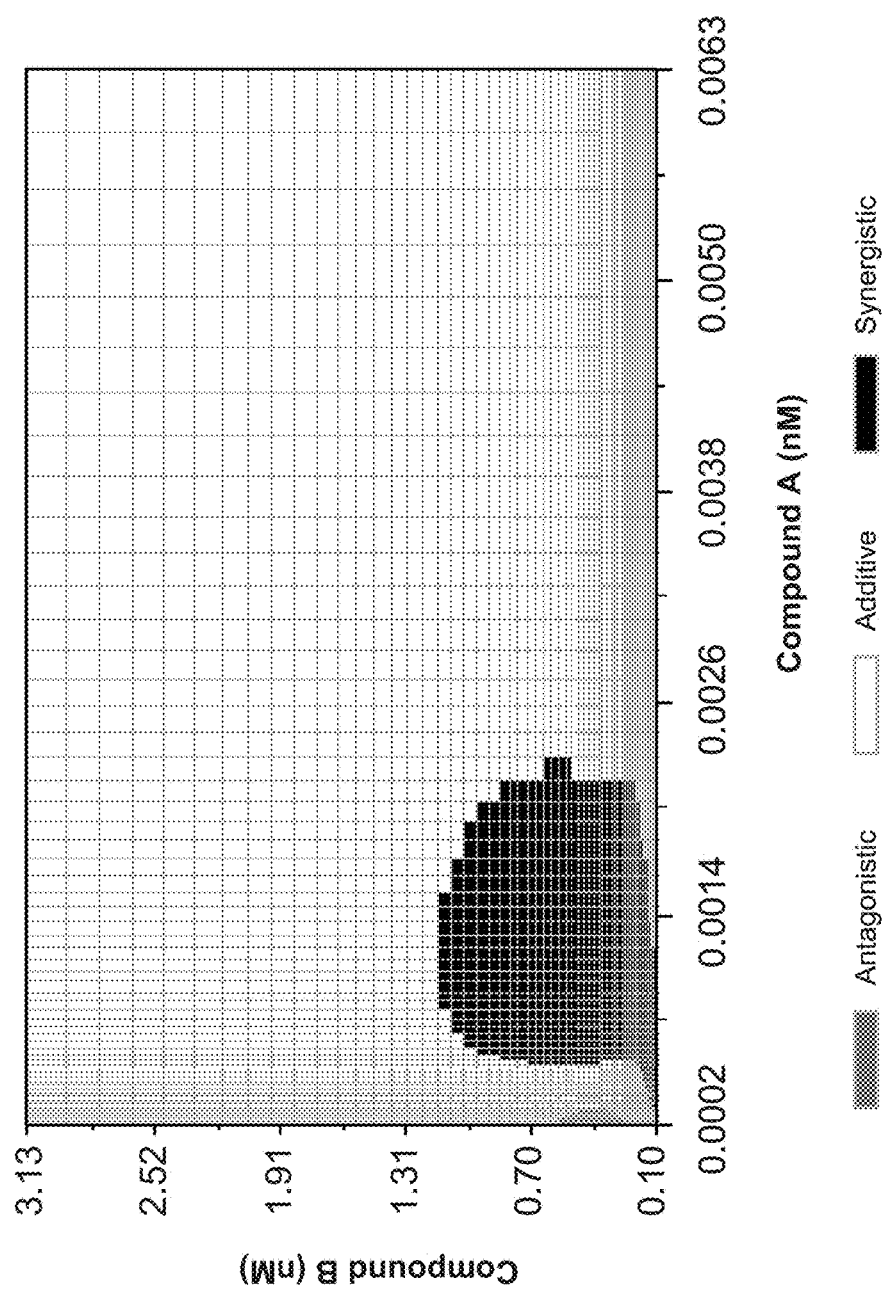
FIG. 2 is a two-dimensional contour plot illustrating the statistically significant synergistic, additive or antagonistic anti-HCV effects at various concentrations of the combination of compound A and compound B in the HCV Genotype 1b (Con1) replicon using the Prichard and Shipman model as a reference.

The results of the replicon assay analysis using the Prichard-Shipman Model are illustrated in Table 1 and in FIGS. 1 and 2.

Table 1 below lists various combinations of concentrations of compound A and compound B. For each combination of concentrations, Table 1 includes the mean difference in the observed and predicted fraction of inhibition, the standard deviation or error of the mean difference, and the upper and lower limits of the 95% confidence interval of the mean difference between observed and predicted fractions of inhibition.

TABLE 1

| Compound A, nM | Compound B, nM | Mean difference in fraction of inhibition: Observed − Predicted | Standard error of mean difference | Lower 95% confidence limit | Upper 95% confidence limit |
| --- | --- | --- | --- | --- | --- |
| 0.000195 | 0.390625 | −0.16428 | 0.054657 | −0.29032 | −0.03824 |
| 0.000391 | 0.097656 | 0.17174 | 0.035597 | 0.08929 | 0.25420 |
| 0.000781 | 0.097656 | 0.16218 | 0.063815 | 0.01502 | 0.30933 |
| 0.000781 | 0.195313 | 0.13851 | 0.054433 | 0.01298 | 0.26403 |
| 0.000781 | 0.390625 | 0.09246 | 0.021657 | 0.04252 | 0.14240 |
| 0.000781 | 0.781250 | 0.08495 | 0.016567 | 0.04674 | 0.12315 |
| 0.001563 | 0.195313 | 0.07811 | 0.032016 | 0.00417 | 0.15205 |
| 0.001563 | 0.390625 | 0.05619 | 0.016132 | 0.01900 | 0.09339 |
| 0.001563 | 0.781250 | 0.05043 | 0.012437 | 0.02175 | 0.07911 |

According to Table 1, all but one of the concentration combinations of compound A and compound B listed in the table have statistically significant synergistic effects.

FIG. 1 illustrates deviations from expected interactions between compound A and compound B are purely additive at concentrations associated with a horizontal plane at 0%. Synergistic interactions between compound A and compound B appear as a peak above the horizontal plane with a height corresponding to the percent above calculated additivity. Antagonistic interactions between compound A and compound B appear as a pit or trough below the horizontal plane with a negative value signifying the percent below the calculated additivity. It is apparent from FIG. 1 that synergistic interactions between compound A and compound B exist at many of the concentration combinations of compounds A and B.

The contour plot of FIG. 2 displays the region of concentration combinations with a statistically significant synergistic, antagonistic, or additive effect. Synergistic interactions appear as dark grey, additive interactions appear white, and antagonistic interactions appear as light grey. As illustrated in FIG. 2, an additive or synergistic effect exists at most of the concentrations for compound A and compound B. In particular, there is a concentration region showing synergy at the lower dose concentrations of compounds A and B.

The results presented in Table 1 and FIGS. 1 and 2 demonstrate that the combination of therapeutic agent A and therapeutic agent B achieves additivity or synergy at most concentration combinations of therapeutic agent A and therapeutic agent B. Taken together, these in vitro replicon results suggest that therapeutic agent A should produce a significant antiviral effect in patients when administered in combination with therapeutic agent B in patients infected with HCV.

Colony Counting Assay

Replicon colonies were exposed to therapeutic agent A, therapeutic agent B, an HCV protease inhibitor (a macrocyclic compound comprising a 9-membered fused bicycle, herein referred to as "therapeutic agent C"), and various combinations of these agents, to quantify the frequency of resistance of these replicon colonies to these agents.

The stable subgenomic bicistronic replicon cell line derived from HCV genotype 1a (H77; Genbank accession number AF011751) was generated by introducing the constructs into cell lines derived from the human hepatoma cell line Huh-7. The replicon also contains a firefly luciferase reporter and a neomycin phosphotransferase (Neo) selectable marker. The first cistron and the second cistron of the bicistronic replicon construct are separated by the FMDV 2a protease, and the second cistron comprises the HCV NS3-NS5B coding region with addition of adaptive mutations E1202G, K1691R, K2040R and S2204I.

The HCV replicon cell line was maintained in Dulbecco's modified Eagles medium (DMEM; Invitrogen) containing 10% (v/v) fetal bovine serum, 100 IU/ml penicillin, 100 µg/ml streptomycin, and 200 µg/ml G418 (all from Invitrogen). 1a-H77 replicon cells ($10^5$-$10^6$) were plated in 150 mm cell culture plates and grown in the presence of G418 (400 µg/ml) and therapeutic agent A, the potassium salt of compound B and/or therapeutic agent C at concentrations that were either 10-fold or 100-fold above the $EC_{50}$ value for the HCV genotype 1a replicon cell line. After three weeks of treatment, the majority of replicon cells were cleared of replicon RNA and, therefore, were unable to survive in the G418-containing medium. The cells containing resistant replicon variants survived and formed colonies. These colonies were stained with 1% crystal violet in 10% Protocol SafeFix II reagent (Fisher Scientific) and counted.

Figure 3:
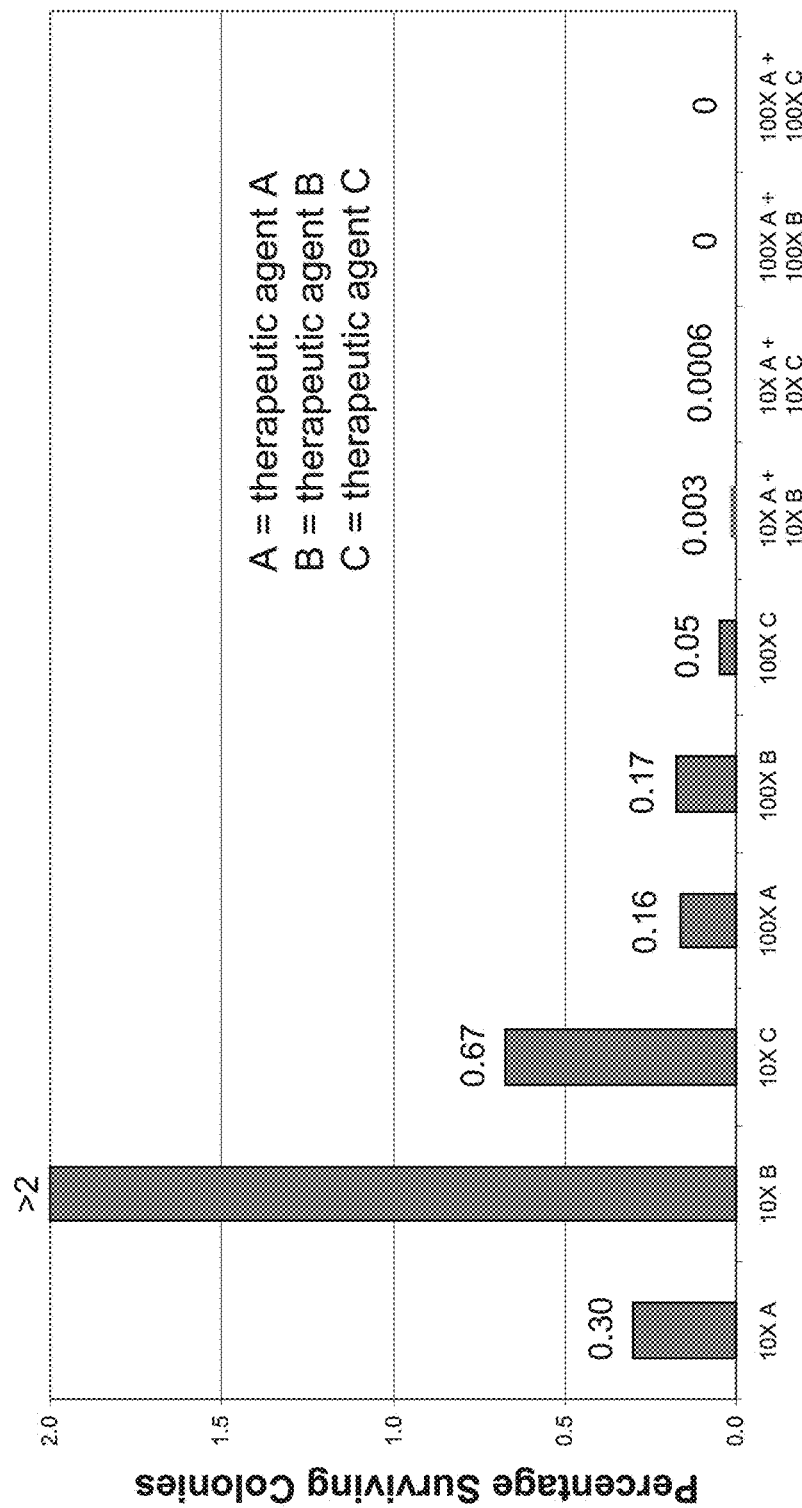
FIG. 3 is a bar graph illustrating the percentage of replicon colonies surviving exposure to various concentrations of therapeutic agent A, therapeutic agent B and therapeutic agent C in a replicon colony count assay.

As shown in FIG. 3, the combination of therapeutic agent A and therapeutic agent B, and the combination of therapeutic agent A and therapeutic agent C, at concentrations either 10-fold or 100-fold above their respective $EC_{50}$ values, resulted in significantly fewer colonies than therapeutic agent A, therapeutic agent B or therapeutic agent C alone at concentrations 10-fold or 100-fold above their respective $EC_{50}$ values.

All references (patent and non-patent) cited above are incorporated by reference into this patent application. The discussion of those references is intended merely to summarize assertions made by their authors. No admission is made that any reference (or a portion of a reference) is relevant prior art (or prior art at all). Applicants reserve the right to challenge the accuracy and pertinence of the cited references.

We claim:

1. A method for treating a subject infected with hepatitis C virus (HCV) genotype 1, said method comprising administering to said subject an amount of therapeutic agent A and an amount of therapeutic agent B, wherein therapeutic agent A is compound A or a salt thereof:

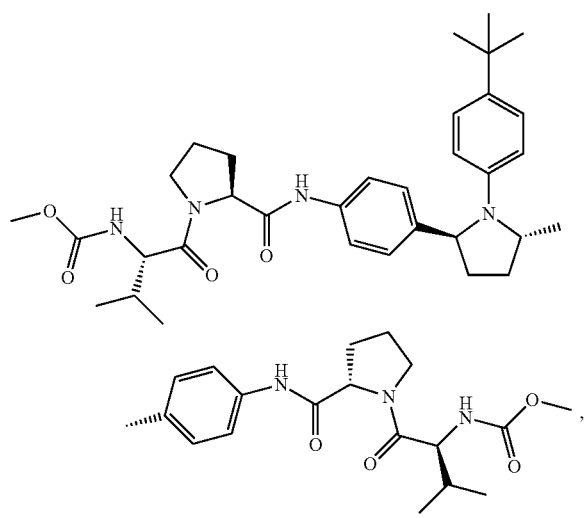

wherein therapeutic agent B is compound B or a salt thereof:

compound B

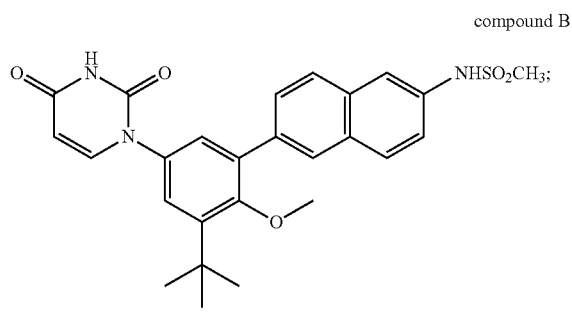

wherein the molar ratio of therapeutic agent A to therapeutic agent B is about 1:20 to about 1:2000, and wherein therapeutic agent A and therapeutic agent B are administered to the subject from the same pharmaceutical composition.

2. The method of claim 1, wherein the subject is a human.

3. The method of claim 1, wherein the total daily dosage amount of therapeutic agent A administered to the subject is about 25 mg.

4. The method of claim 1, wherein therapeutic agent B is a sodium salt of compound B.

5. The method of claim 1, wherein the method further comprises administering one or more additional therapeutic agents selected from the group consisting of interferon, ribavirin, taribavirin, and HCV inhibitor.

6. The method of claim 5, wherein the additional therapeutic agent is an HCV inhibitor.

7. The method of claim 6, wherein the HCV inhibitor is an HCV protease inhibitor.

8. The method of claim 5, wherein therapeutic agent A, therapeutic agent B, and the additional therapeutic agent are administered to the subject from the same pharmaceutical composition.

9. The method of claim 3, wherein the pharmaceutical composition is administered to the subject once is a 24-hour period.

10. The method of claim 7, wherein the method further comprises administering a cytochrome P-450 inhibitor.

11. The method of claim 10, wherein the cytochrome P-450 inhibitor is ritonavir.

12. The method of claim 1, wherein the total daily dosage of both therapeutic agent A and therapeutic agent B are administered to the subject within a twenty-four hour period.

13. The method of claim 12, wherein the pharmaceutical composition is administered once or twice daily.

* * * * *